United States Patent
Korman et al.

(10) Patent No.: US 12,343,045 B2
(45) Date of Patent: Jul. 1, 2025

(54) TARGETING GUIDE AND ASSOCIATED METHOD

(71) Applicant: WRIGHT MEDICAL TECHNOLOGY, INC., Memphis, TN (US)

(72) Inventors: Zachary Korman, Memphis, TN (US); John White, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 341 days.

(21) Appl. No.: 17/759,627

(22) PCT Filed: Nov. 6, 2020

(86) PCT No.: PCT/US2020/059351
§ 371 (c)(1),
(2) Date: Jul. 28, 2022

(87) PCT Pub. No.: WO2021/201916
PCT Pub. Date: Oct. 7, 2021

(65) Prior Publication Data
US 2023/0055767 A1   Feb. 23, 2023

Related U.S. Application Data

(60) Provisional application No. 63/001,610, filed on Mar. 30, 2020.

(51) Int. Cl.
*A61B 17/06* (2006.01)
*A61B 17/17* (2006.01)
(Continued)

(52) U.S. Cl.
CPC .......... *A61B 17/66* (2013.01); *A61B 17/1775* (2016.11); *A61B 2017/565* (2013.01); *A61B 2017/681* (2013.01)

(58) Field of Classification Search
CPC ................ A61B 17/17; A61B 17/1775; A61B 2017/565; A61B 17/66; A61B 2017/681;
(Continued)

(56) References Cited

U.S. PATENT DOCUMENTS

| | | |
|---|---|---|
| 4,421,112 A | 12/1983 | Mains et al. |
| 6,358,250 B1 | 3/2002 | Orbay |

(Continued)

FOREIGN PATENT DOCUMENTS

| | | |
|---|---|---|
| CN | 204049714 U | 12/2014 |
| DE | 201010948 U1 | 9/2001 |

(Continued)

OTHER PUBLICATIONS

Mica, Minimally Invasive Foot Surgery, "Chevron Osteotomy Surgical Technique", Wright Medical Technology, Inc., 15 pages, Oct. 17, 2017.
(Continued)

*Primary Examiner* — Larry E Waggle, Jr.
(74) *Attorney, Agent, or Firm* — DUANE MORRIS LLP

(57) ABSTRACT

A system includes a base and a targeting guide coupled to the base. The base includes a first member and a second member. The first member defines a first hole for receiving a first fixation element for coupling the first member to a bone. The second member is pivotably coupled to the first member. The second member defines a second hole and a third hole. The second hole is for receiving a second fixation element for coupling the second member to a bone, and the third hole is for receiving an adjustment member for adjusting an angle between the first member and the second member. The targeting guide extends from a first end to a second end and defines a fourth hole adjacent to the second end of the targeting guide. The fourth hole is sized and configured to receive a fixation device therein.

9 Claims, 47 Drawing Sheets

(51) Int. Cl.
*A61B 17/56* (2006.01)
*A61B 17/66* (2006.01)
*A61B 17/68* (2006.01)

(58) Field of Classification Search
CPC ... A61B 17/848; A61B 17/8897; A61B 17/90; A61B 17/025; A61B 17/6416; A61B 17/8866
See application file for complete search history.

(56) References Cited

U.S. PATENT DOCUMENTS

| | | | |
|---|---|---|---|
| 6,695,847 | B2 | 2/2004 | Bianchetti et al. |
| D549,331 | S | 8/2007 | Tomatsu et al. |
| 7,261,713 | B2* | 8/2007 | Langmaid ............. A61B 17/66 606/59 |
| 7,507,240 | B2* | 3/2009 | Olsen ................ A61B 17/6475 606/57 |
| 8,734,452 | B2* | 5/2014 | Chin .................. A61B 17/8695 606/86 A |
| 8,939,984 | B2* | 1/2015 | Budoff ............... A61B 17/8866 606/88 |
| 11,166,750 | B1* | 11/2021 | Wurapa ............. A61B 17/6416 |
| 11,672,549 | B2* | 6/2023 | Cundiff ............. A61B 17/1775 606/87 |
| 2009/0099571 | A1 | 4/2009 | Cresina et al. |
| 2009/0204148 | A1 | 8/2009 | Lenke et al. |
| 2011/0106086 | A1 | 5/2011 | Laird |
| 2012/0130383 | A1 | 5/2012 | Budoff |
| 2013/0090662 | A1 | 4/2013 | Hanson et al. |
| 2014/0180348 | A1 | 6/2014 | Thoren et al. |
| 2014/0194999 | A1 | 7/2014 | Orbay et al. |
| 2014/0276843 | A1 | 9/2014 | Koay et al. |
| 2015/0071885 | A1 | 3/2015 | Saw et al. |
| 2015/0230822 | A1 | 8/2015 | Hanson et al. |
| 2018/0250024 | A1 | 9/2018 | Woodard et al. |
| 2021/0212704 | A1* | 7/2021 | Wong .................. A61B 17/152 |

FOREIGN PATENT DOCUMENTS

| | | |
|---|---|---|
| JP | S58209343 A | 12/1983 |
| JP | H07184943 A | 7/1995 |
| JP | 3046822 B1 | 5/2000 |
| JP | 2009530053 A | 8/2009 |
| JP | 2013511353 A | 4/2013 |
| JP | 2014131735 A | 7/2014 |
| WO | 2011063257 A1 | 5/2011 |
| WO | 2014000661 A1 | 1/2014 |

OTHER PUBLICATIONS

Ortholic 3Di Ankle Fracture LP Plate System, Tray Layout Guide, Wright Medical Technology, Inc., Jan. 2016, 16 pages.
Office Action issued in connection with corresponding Canadian Patent Application No. 3,100,061, Feb. 8, 2022, 5 pages.
Second Examination Report issued in connection with corresponding Australian Patent Application No. 2018278965, Mar. 25, 2020, 3 pages.
Production Introduction—Innomed Shoulder Instruments—retractors & elevators, <URL.www.innomed.net/shoulder_refs_standard.htm#ShoulderSurgeryRetractorSystemShRets>, Published on Mar. 4, 2014 as per Wayback Machine.
Production Introduction—Innomed Small Bone instruments—Foot & Ankle—retraction & exposure, <URI.www.innomed.net/smallbone_footankle_exposure.htm>. Published on Jan. 7, 2009 as per Wayback Machine.
Office Action issued in connection with corresponding Japanese Patent Application No. 2018-511653, Sep. 10, 2019, 4 pages.
Office Action issued in connection with corresponding Canadian Patent Application No. 2,997,369, Sep. 19, 2019, 3 pages.
International Search Report and Written Opinion issued for PCT/US2016/049981, Dec. 8, 2016.
Partial Search Report issued in connection with corresponding European Patent Application No. 16843015.5, Mar. 19, 2019, 11 pages.
First Office Action issued in connection with corresponding Japanese Patent Application No. 2018-511653, Mar. 12, 2019, 5 pages.
First Examination Report issued in connection with corresponding Australian Patent Application No. 2016317999, Jun. 15, 2016, 6 pages.
International Search Report and Written Opinion issued in connection with International Patent Application No. PCT/US2020/059351, Feb. 4, 2021, 8 pages.

* cited by examiner

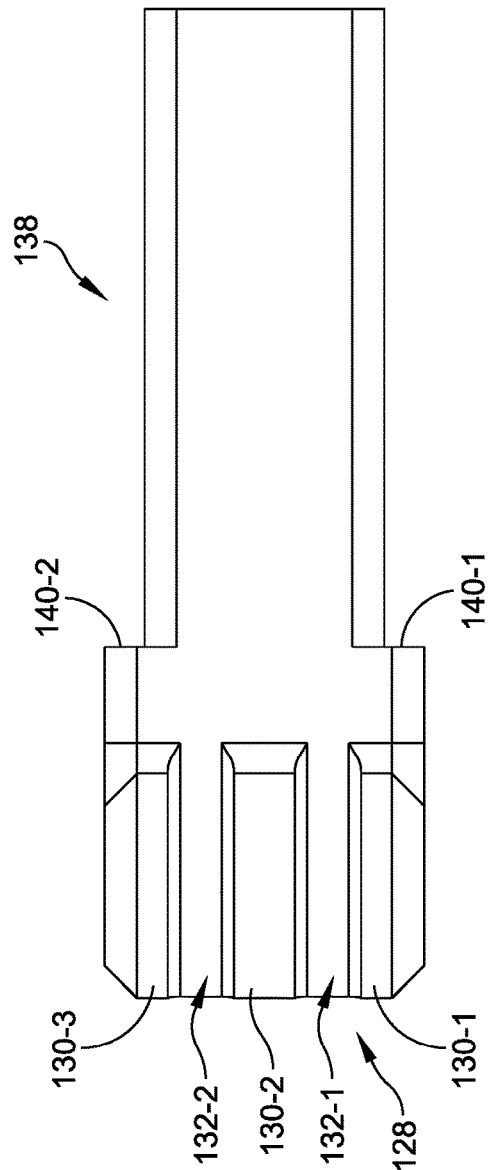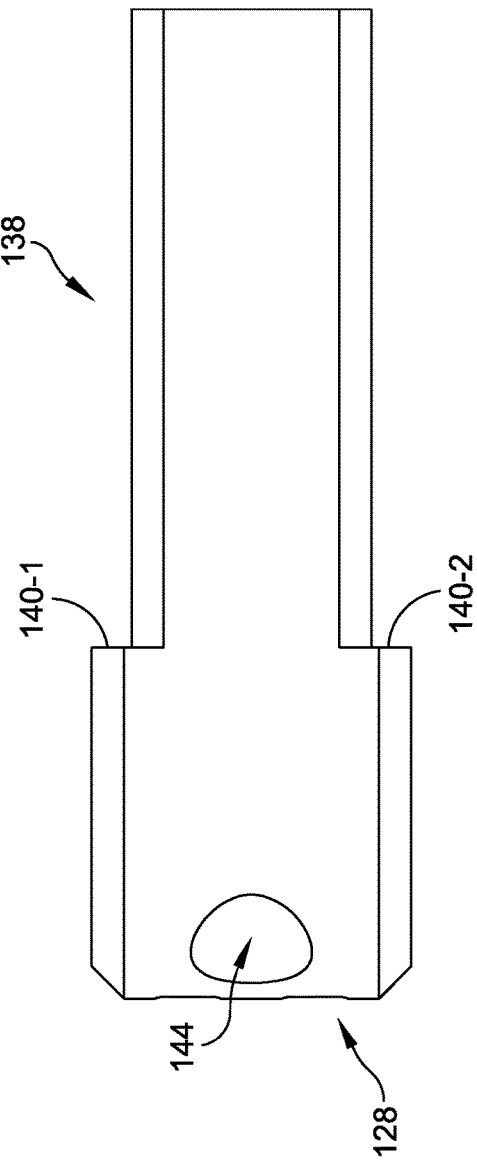

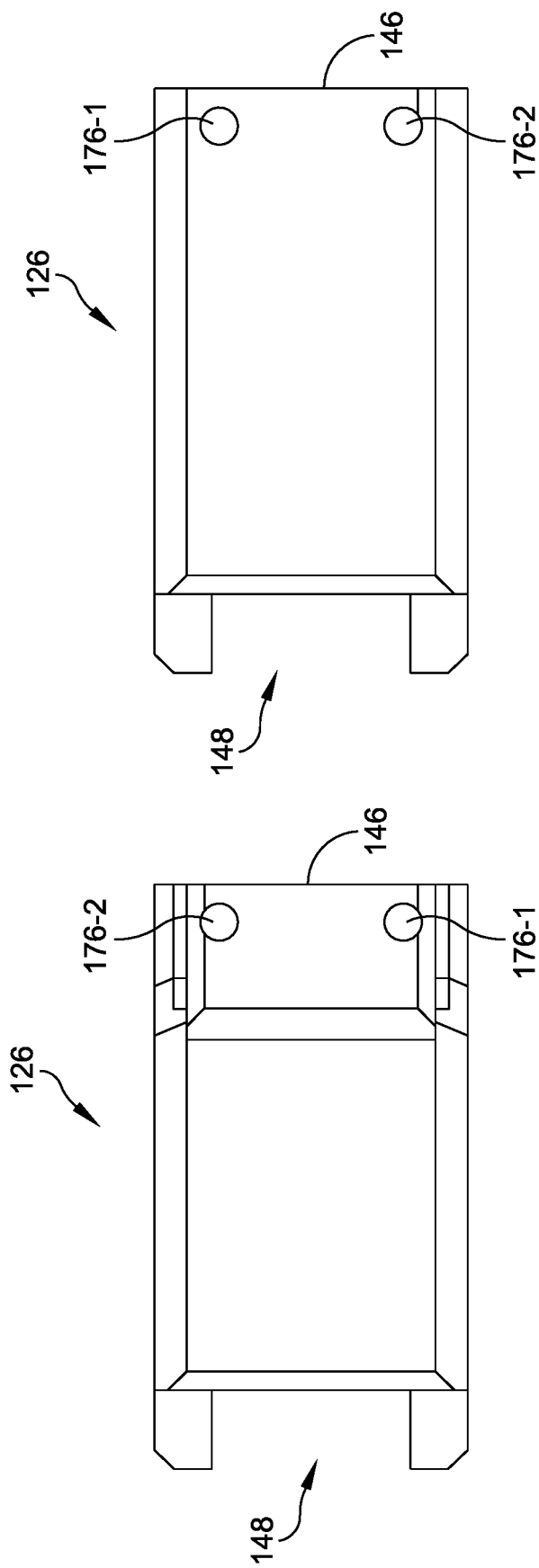

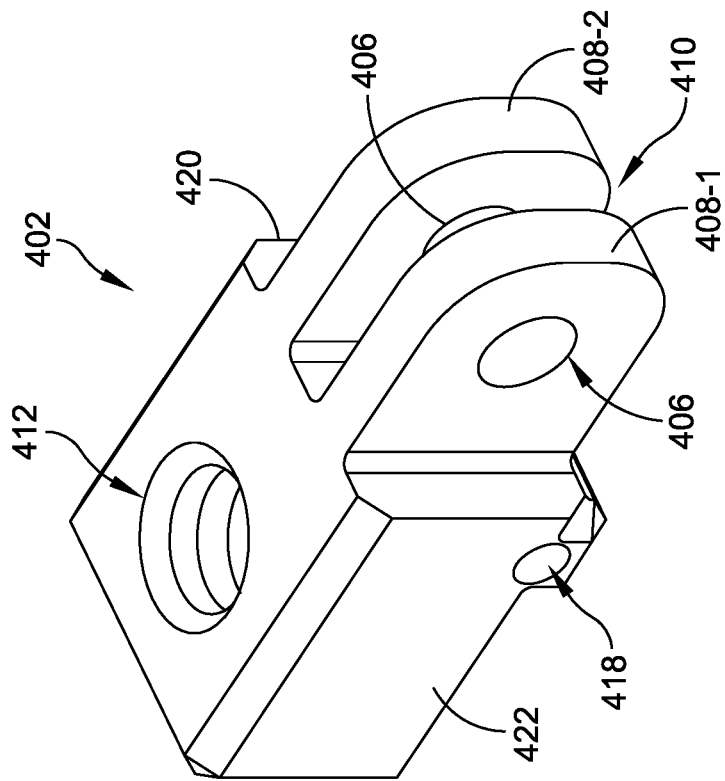
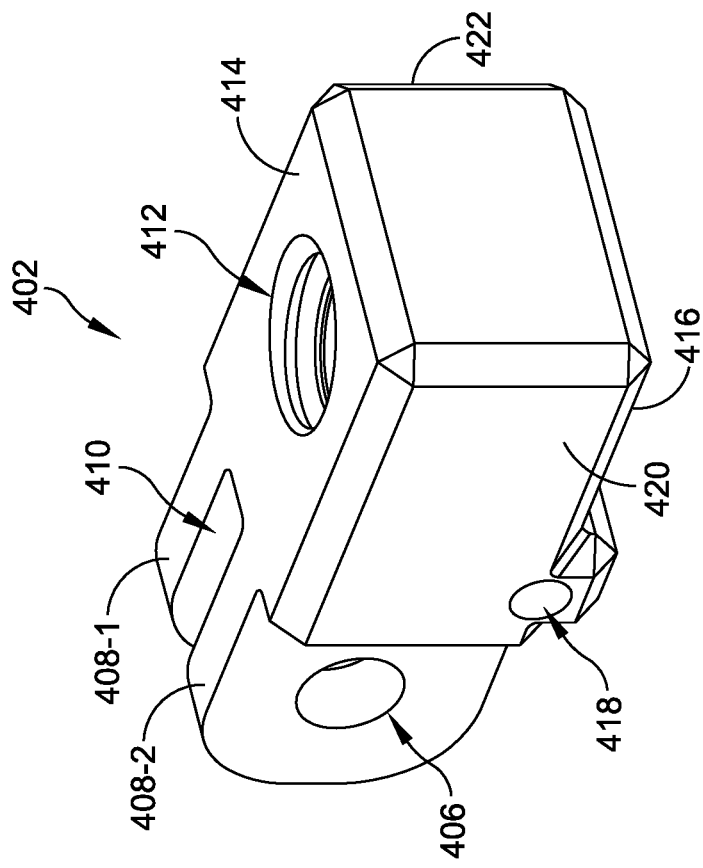
FIG. 28
FIG. 27

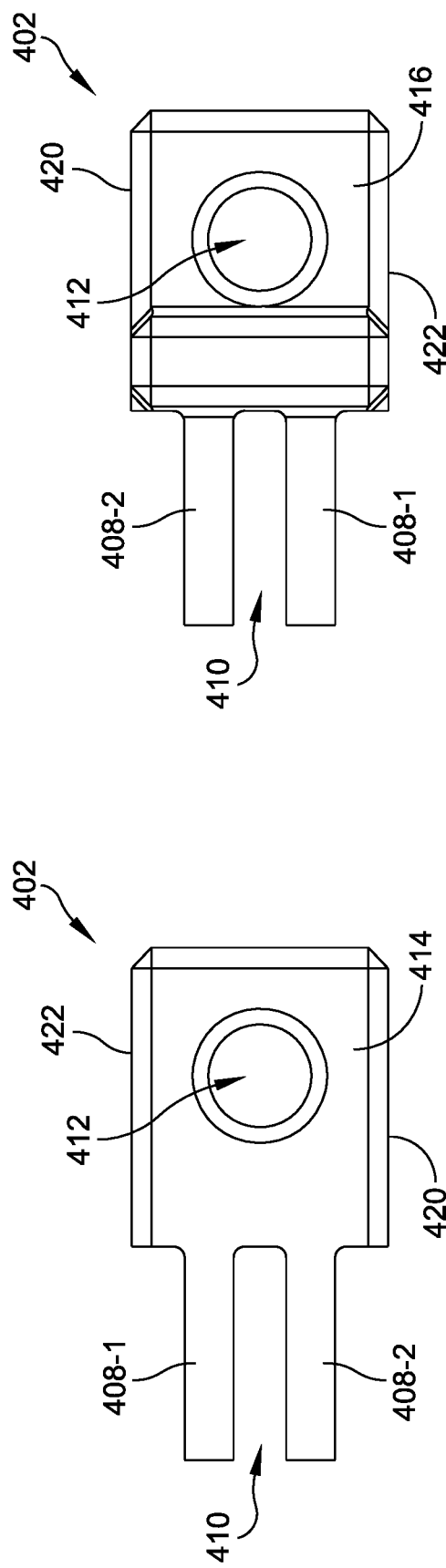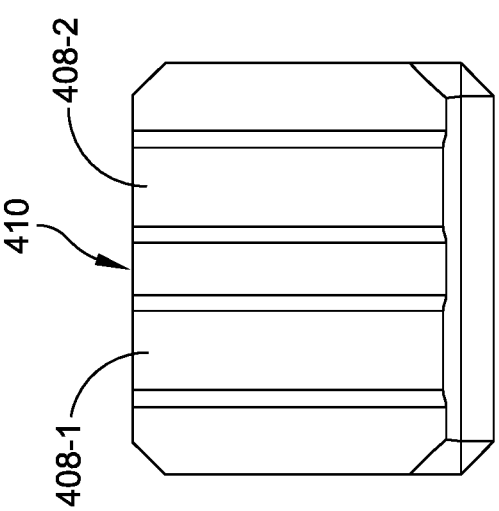

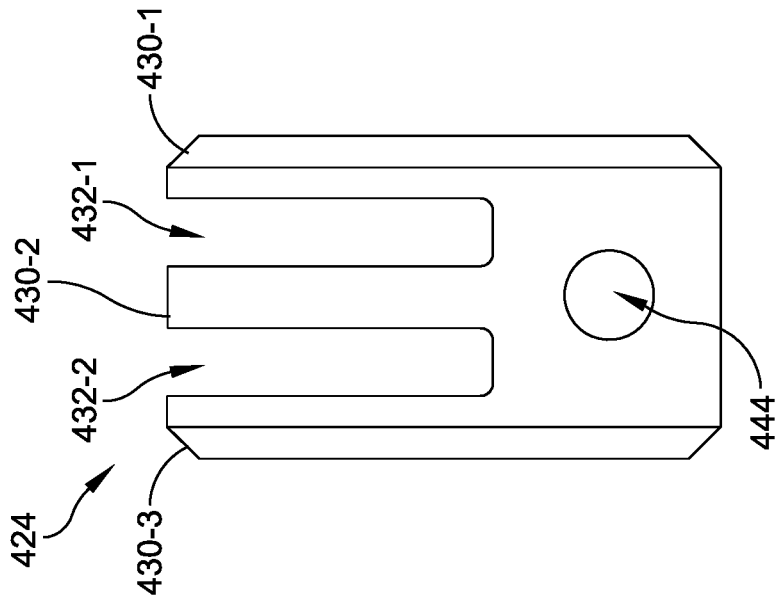
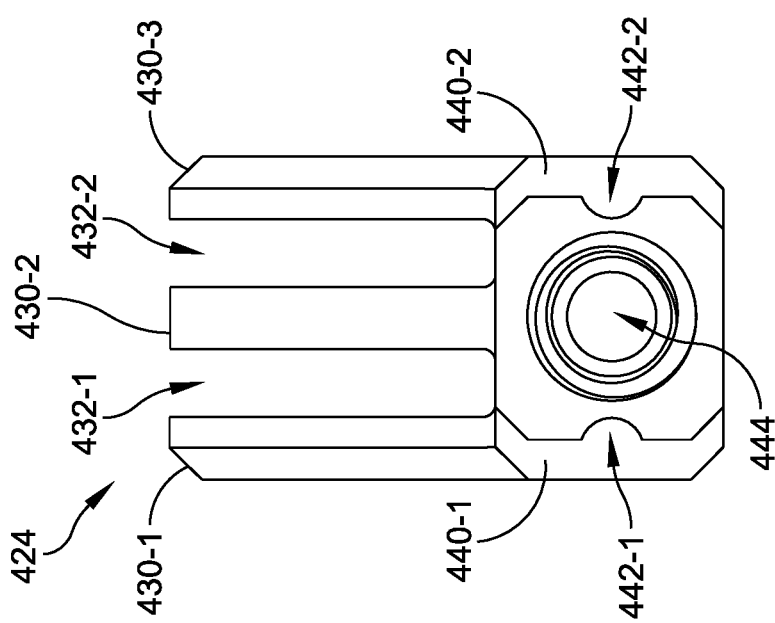

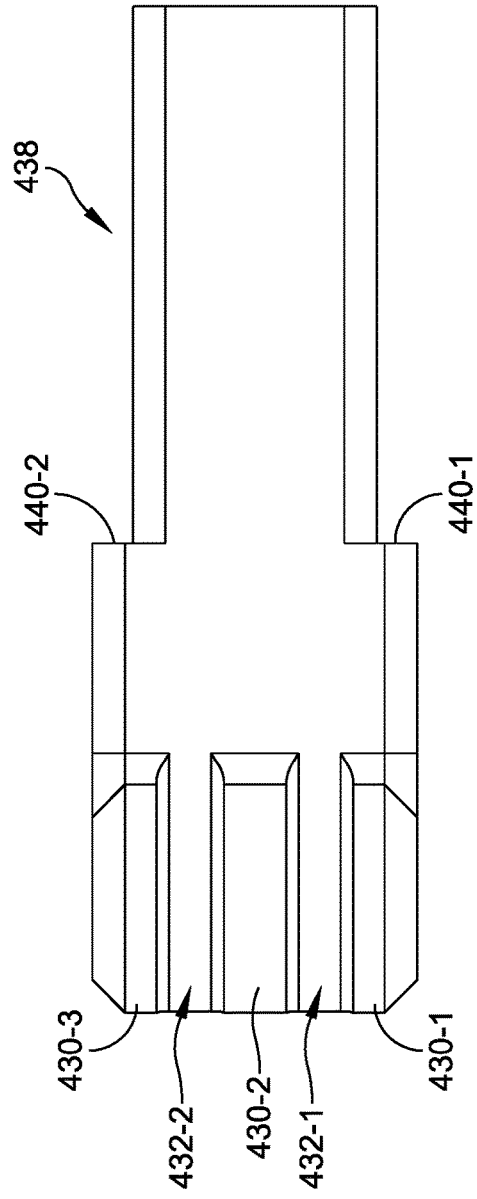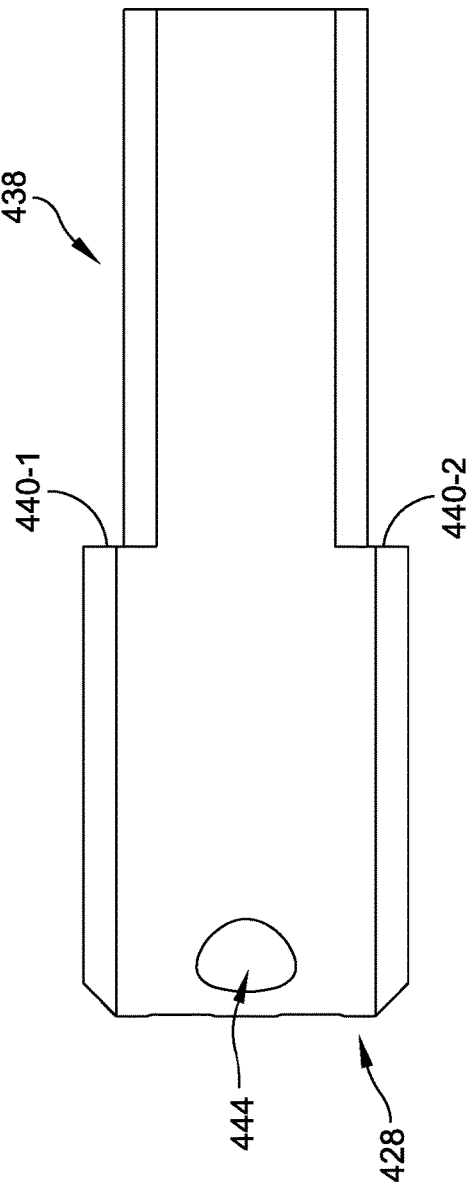

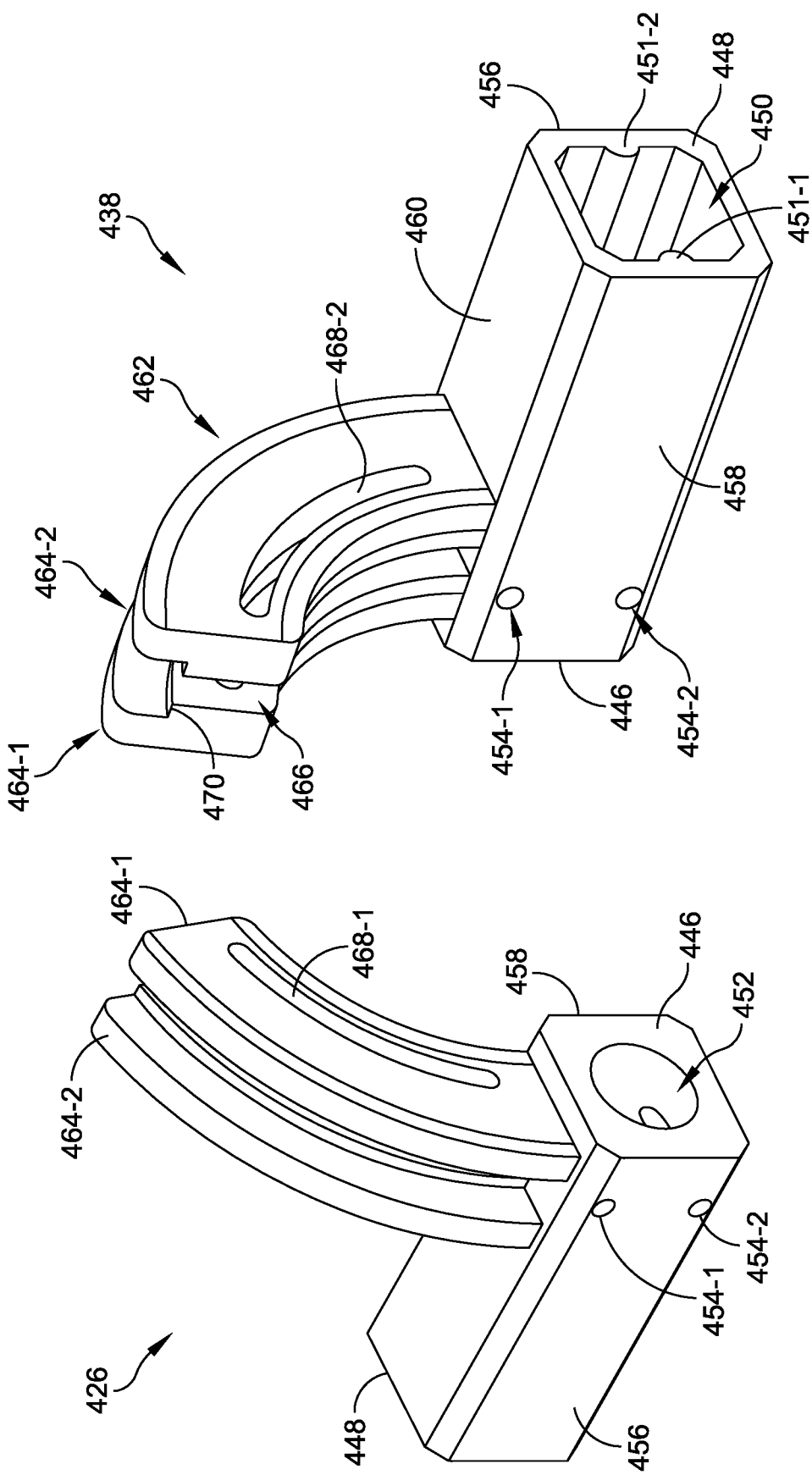

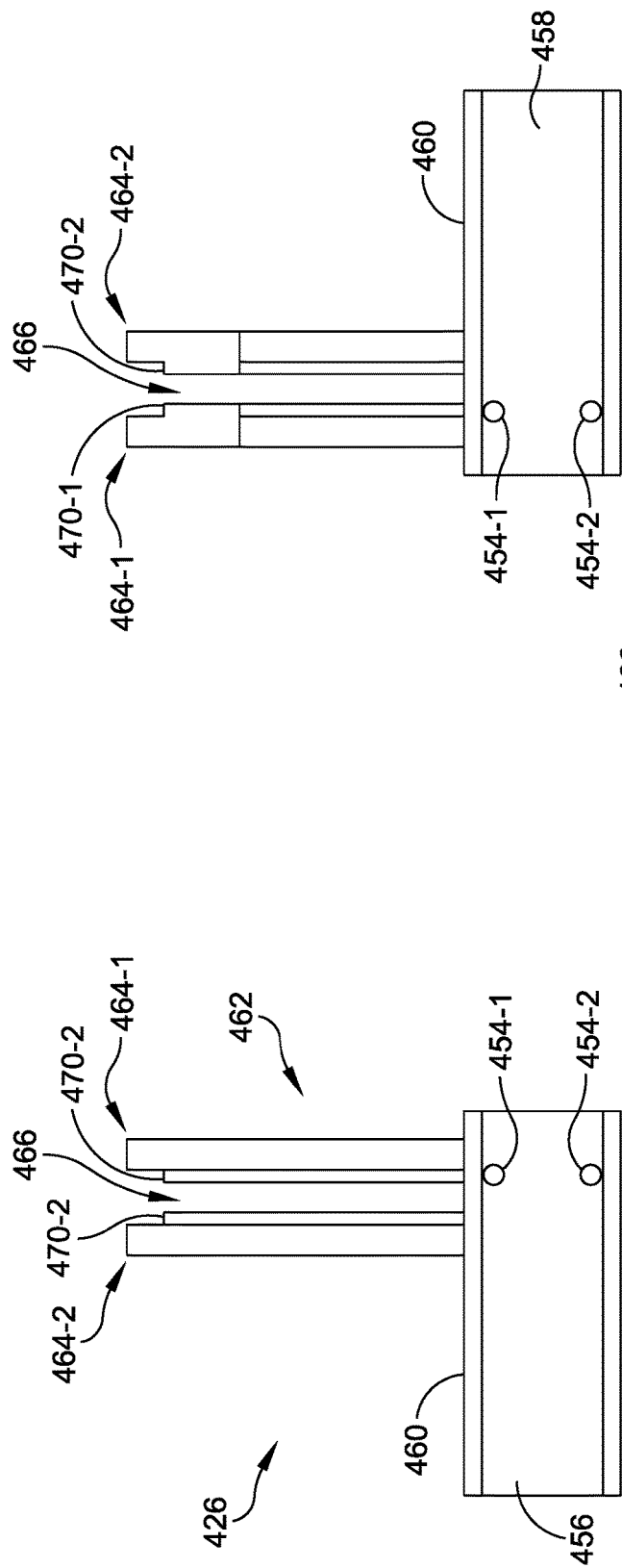
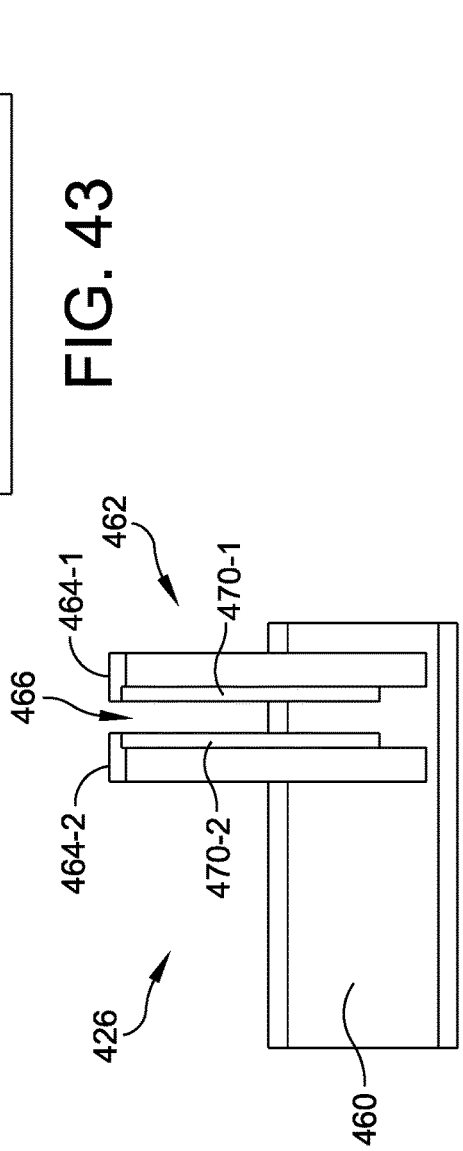
FIG. 42
FIG. 43
FIG. 44

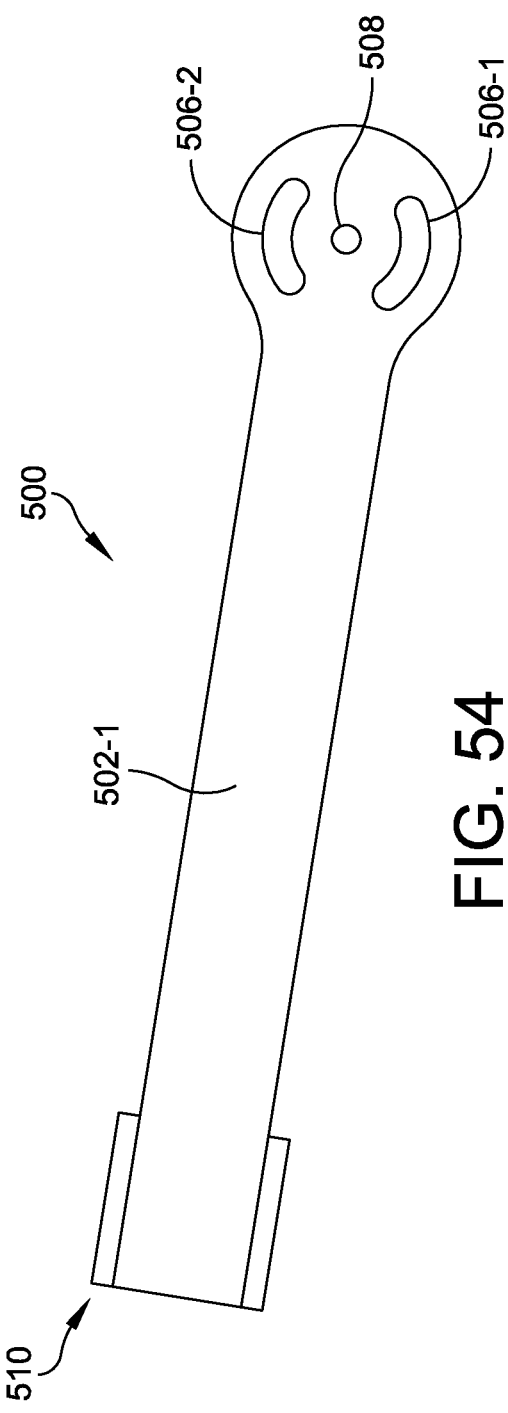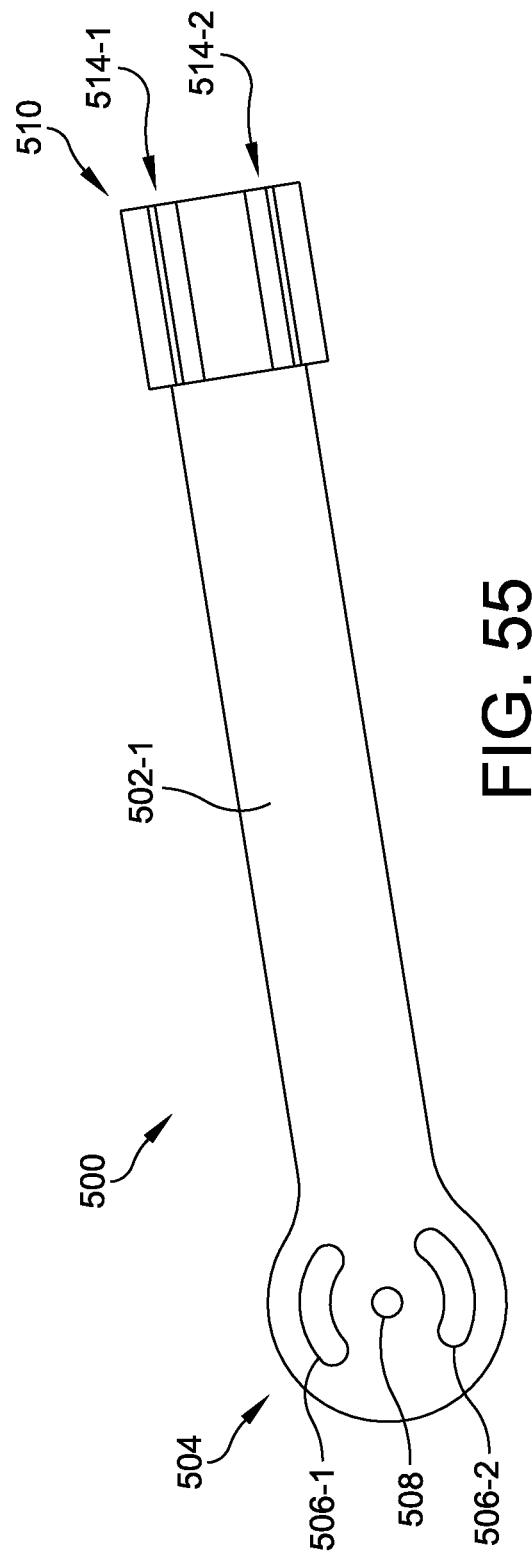

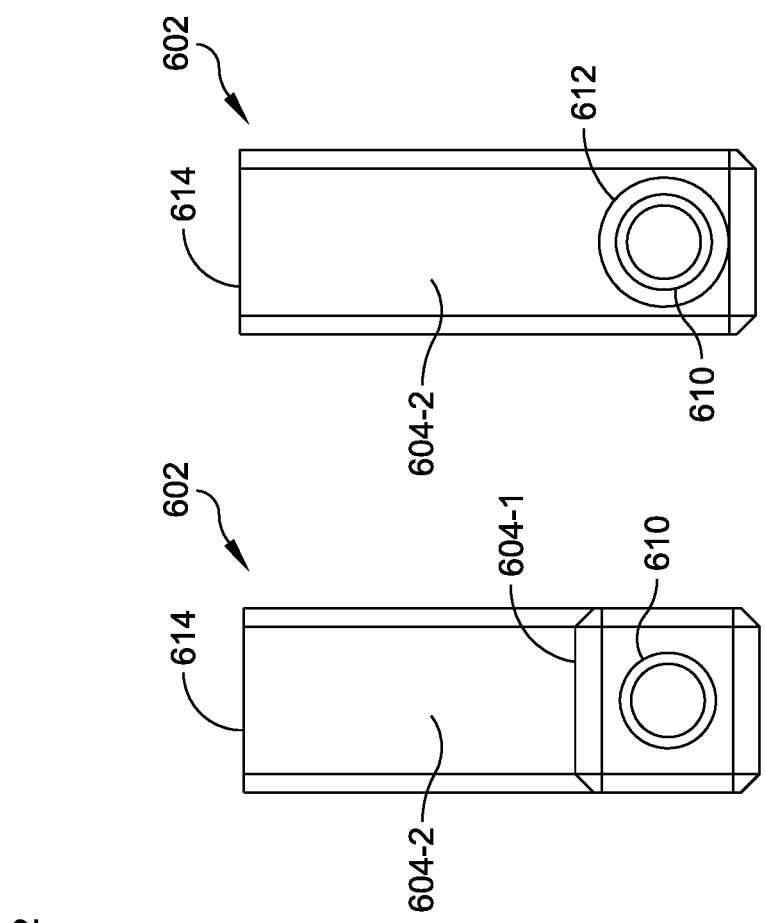
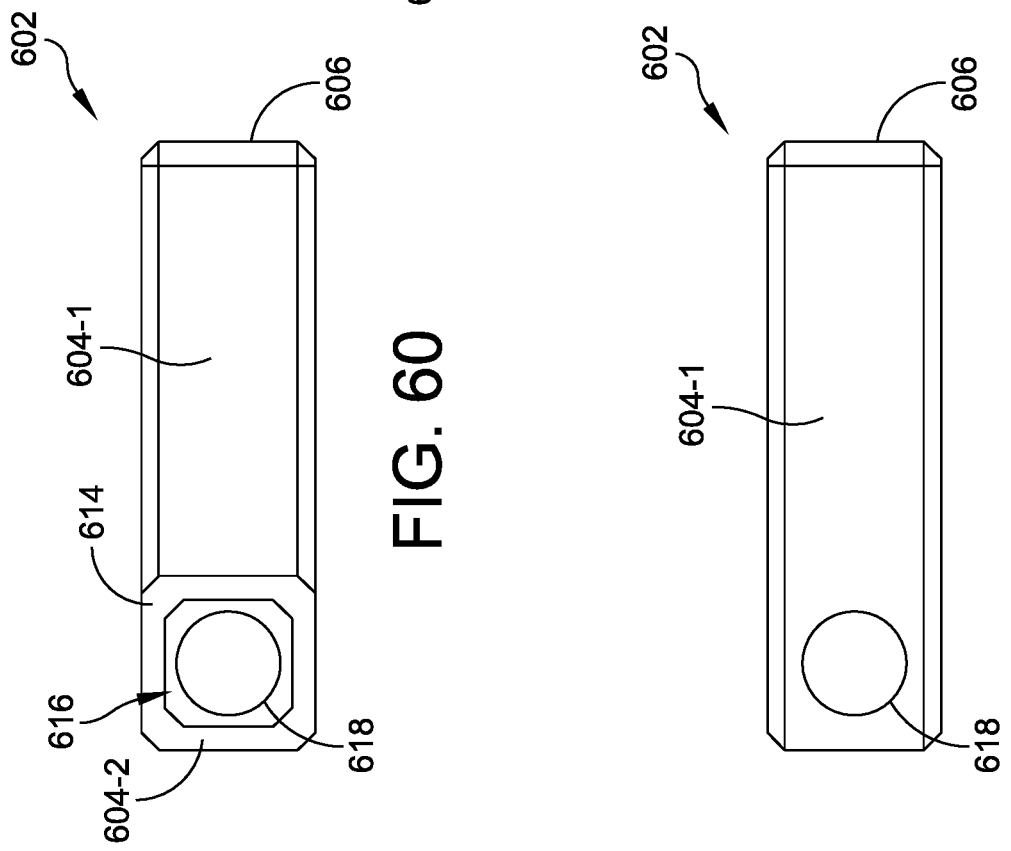

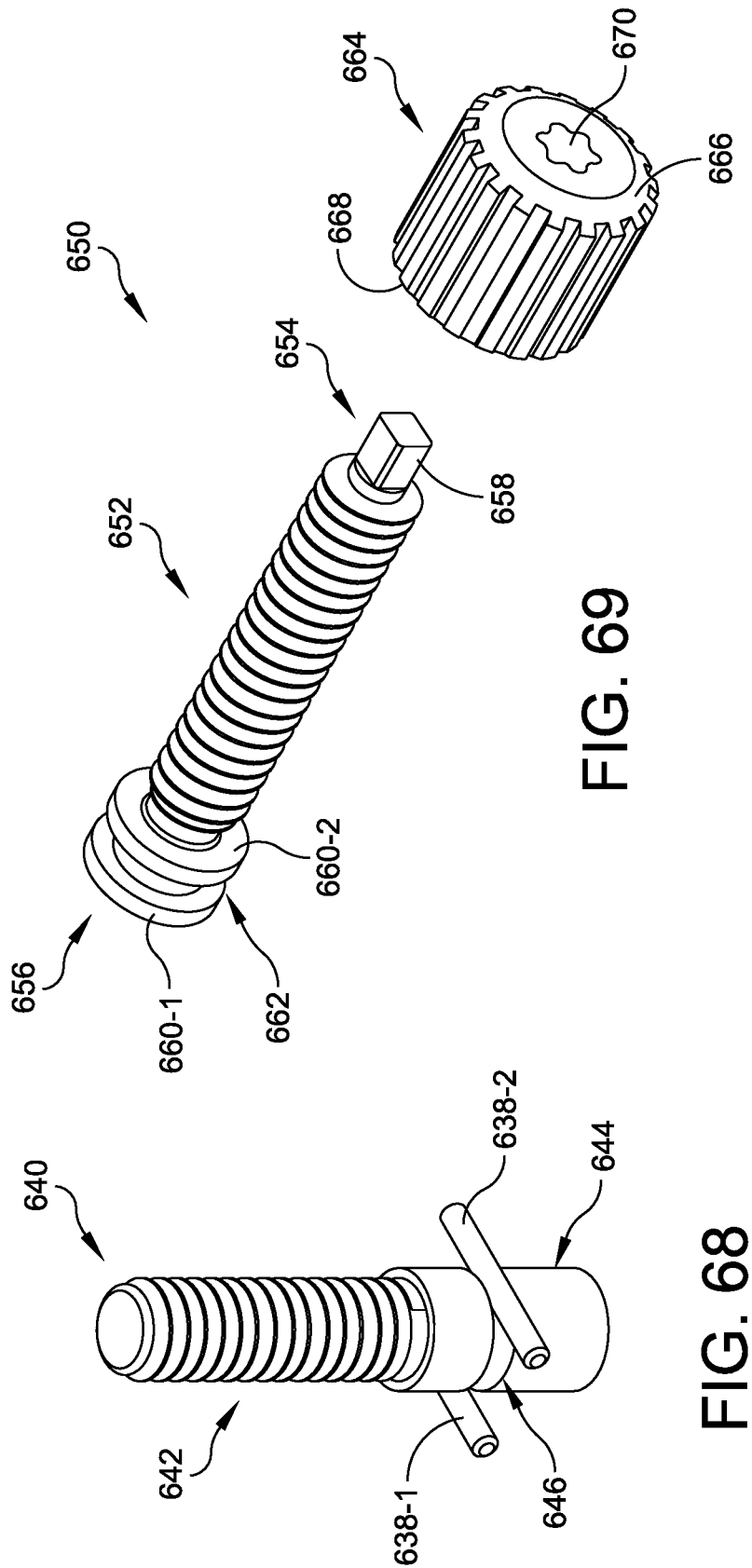

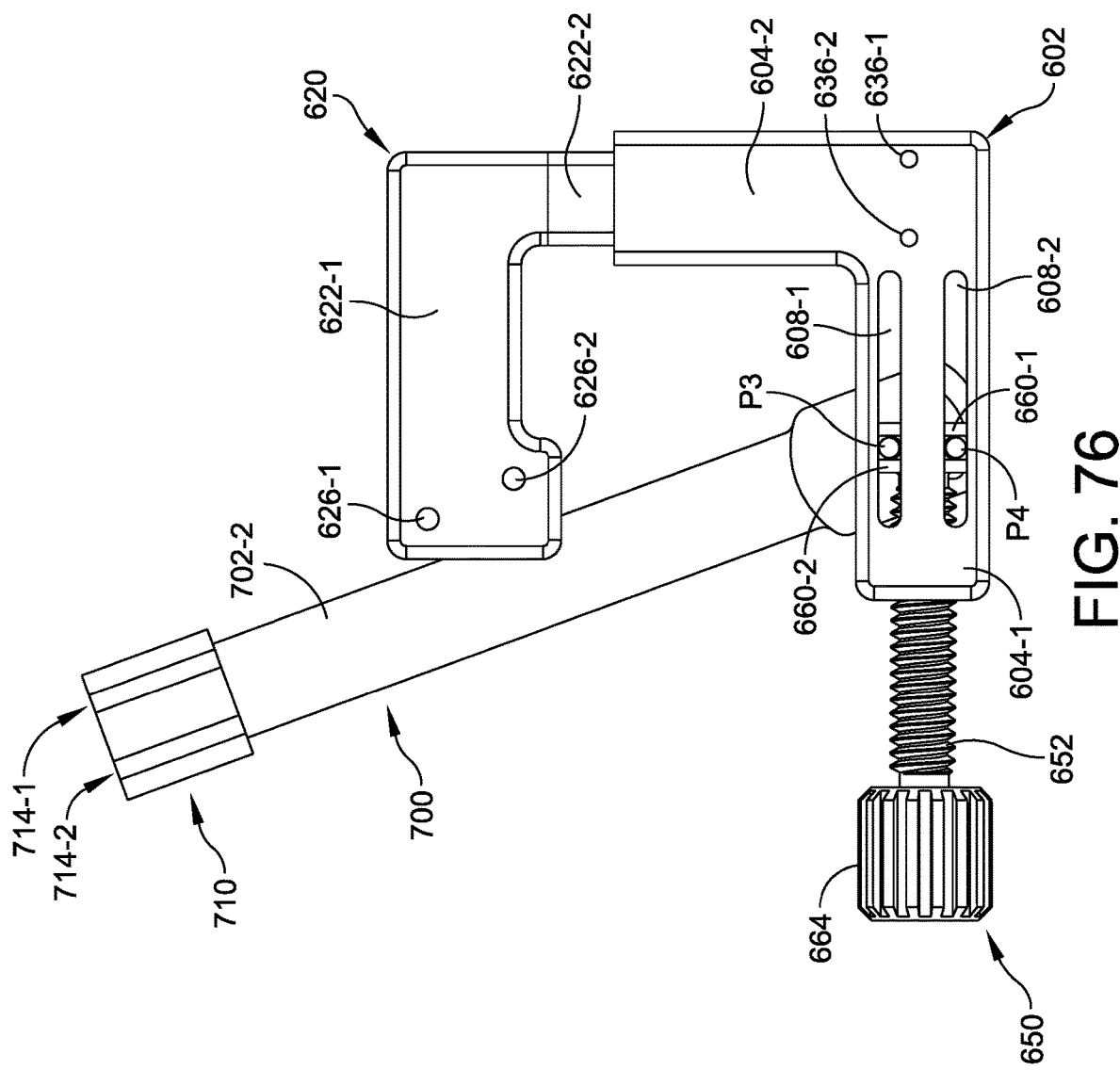

TARGETING GUIDE AND ASSOCIATED METHOD

CROSS-REFERENCE TO RELATED APPLICATIONS

This application is a National Stage Application, filed under 35 U.S.C. 371, of International Patent Application No. PCT/US2020/059351, filed on Nov. 6, 2020, which claims priority to U.S. Provisional Patent Application No. 63/001,610, filed on Mar. 30, 2020, the entireties of which are incorporated herein by reference.

FIELD OF DISCLOSURE

The disclosed system and method relate to the field of correcting anatomical structures. More particularly, the disclosed systems and methods relate to correcting defects in anatomical structures in the lower extremities of a patient.

BACKGROUND

Hallux valgus deformities (also known as bunions) occur when a metatarsal goes into a varus state (i.e., is pointed inwardly). In addition to being pointed inward, the metatarsal also may be rotated about its longitudinal axis such that the bottom of the bone is facing outwardly, which may result in the sesamoid being pointed outwardly when it should be located underneath the metatarsal. Correction of a bunion typically requires surgery, such as a digital metatarsal osteotomy, to fuse the TMT1 joint (i.e., the joint between the first metatarsal and first cuneiform).

SUMMARY

In some embodiments, a system includes a base and a targeting guide coupled to the base. The base includes a first member and a second member. The first member defines a first hole for receiving a first fixation element for coupling the first member to a bone. The second member is pivotably coupled to the first member. The second member defines a second hole and a third hole. The second hole is for receiving a second fixation element for coupling the second member to a bone, and the third hole is for receiving an adjustment member for adjusting an angle between the first member and the second member. The targeting guide extends from a first end to a second end and defines a fourth hole adjacent to the second end of the targeting guide. The fourth hole is sized and configured to receive a fixation device therein.

In some embodiments, a system includes a base and a targeting member configured to be positioned relative to the base. The base includes first and second members that are coupled together in a pivoting arrangement. The first member includes a first hole for receiving a first fixation element for coupling the first member to a first bone portion and a second hole for receiving an adjustment member for adjusting an angle between the first and second members. The second member has an adjustable length and defines at least one hole for receiving at least one second fixation element for coupling the second member to a second bone portion. The targeting member defines at least one hole for guiding at least one third fixation element into engagement with the first and second bone portions.

In some embodiments, a method includes inserting a first fixation element through a first hole defined by a first member of a base of a tool; inserting a second fixation element through a second hole defined by a second member of the base of the tool; adjusting an angle between the first member and the second member with a first adjustment member; and positioning a targeting member relative to the tool such that the first fixation element is at least partially received within a first hole defined adjacent to a first end of the targeting member.

BRIEF DESCRIPTION OF THE DRAWINGS

FIG. 11 is a top side view of the component illustrated in FIG. 7 in accordance with some embodiments;

FIG. 12 is a bottom side view of the component illustrated in FIG. 7 in accordance with some embodiments;

FIG. 15 is a top side view illustrated in FIG. 13 in accordance with some embodiments;

FIG. 16 is a bottom side view illustrated in FIG. 13 in accordance with some embodiments;

FIG. 27 is a front-side isometric view of a first component of the base illustrated in FIG. 26 in accordance with some embodiments;

FIG. 28 is a rear-side isometric view of the first component illustrated in FIG. 27 in accordance with some embodiments;

FIG. 29 is a top side view of the first component illustrated in FIG. 27 in accordance with some embodiments;

FIG. 30 is a bottom side view of the first component illustrated in FIG. 27 in accordance with some embodiments;

FIG. 31 is a rear side view of the first component illustrated in FIG. 27 in accordance with some embodiments;

FIG. 34 is a front side view of the second component illustrated in FIG. 32 in accordance with some embodiments;

FIG. 35 is a rear side view of the second component illustrated in FIG. 32 in accordance with some embodiments;

FIG. 36 is a top side view of the second component illustrated in FIG. 32 in accordance with some embodiments;

FIG. 37 is a bottom side view of the second component illustrated in FIG. 32 in accordance with some embodiments;

FIG. 38 is a front side isometric view of a third component of the base illustrated in FIG. 26 in accordance with some embodiments;

FIG. 39 is a rear side isometric view of the third component illustrated in FIG. 38 in accordance with some embodiments;

FIG. 42 is a side view of the third component illustrated in FIG. 38 in accordance with some embodiments;

FIG. 43 is a side view opposite of that shown in FIG. 42 of the third component illustrated in FIG. 38 in accordance with some embodiments;

FIG. 44 is a top side view of the third component illustrated in FIG. 38 in accordance with some embodiments;

FIG. 54 is a top side view of the targeting guide illustrated in FIG. 53 in accordance with some embodiments;

FIG. 55 is a bottom side view of the targeting guide illustrated in FIG. 53 in accordance with some embodiments;

FIG. 60 is a top side view of the component shown in FIG. 58 in accordance with some embodiments;

FIG. 61 is a bottom side view of the component shown in FIG. 58 in accordance with some embodiments;

FIG. 62 is a front side view of the component shown in FIG. 58 in accordance with some embodiments;

FIG. 63 is a rear side view of the component shown in FIG. 58 in accordance with some embodiments;

FIG. 68 is an isometric view of one example of an adjustment bolt and cross-pins in accordance with some embodiments;

FIG. 69 is an exploded isometric view of another example of an adjustment bolt in accordance with some embodiments;

FIG. 76 is a side view of the system shown in FIG. 56 in accordance with some embodiments.

DETAILED DESCRIPTION

This description of the exemplary embodiments is intended to be read in connection with the accompanying drawings, which are to be considered part of the entire written description.

Figure 1:
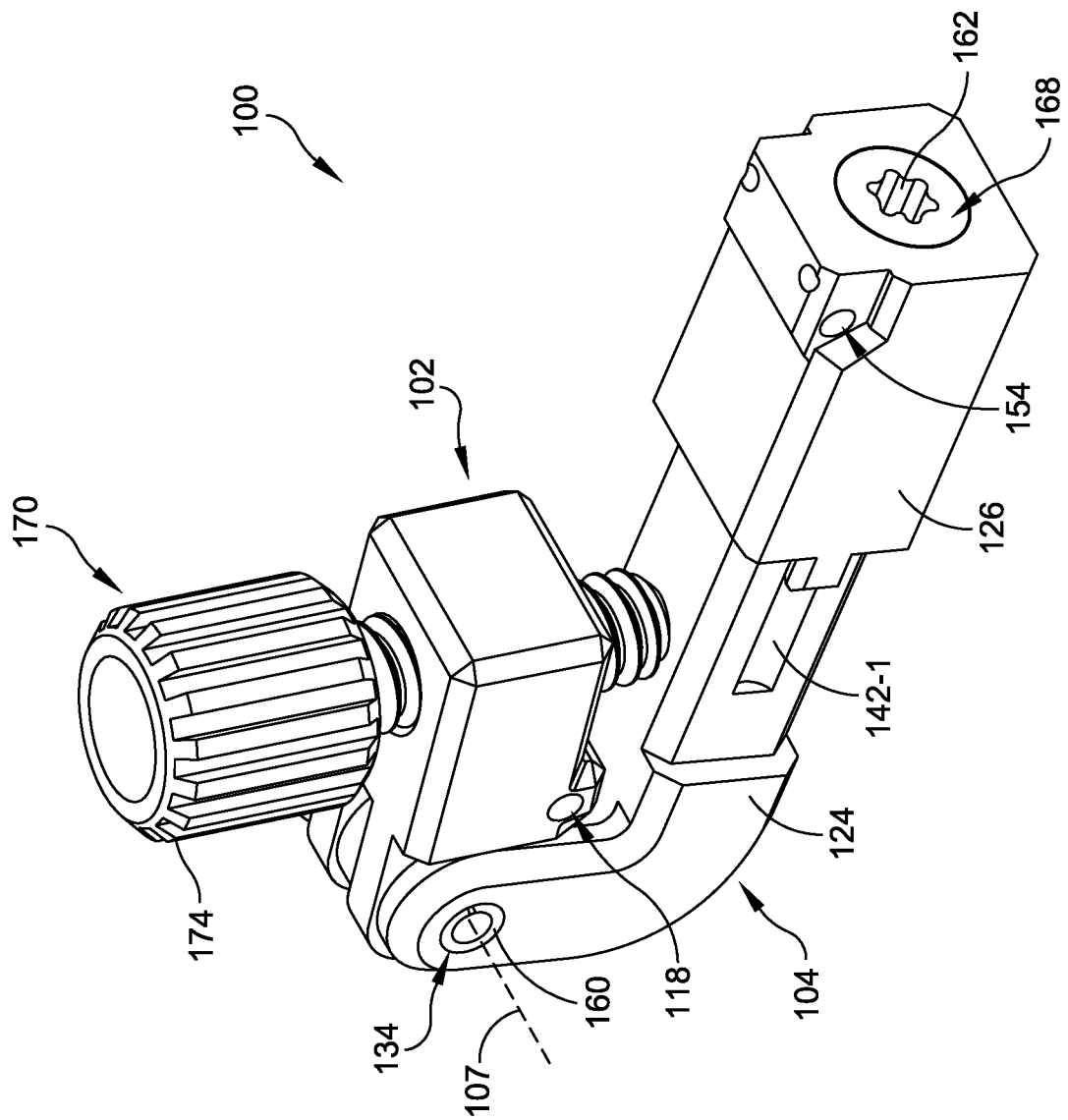
FIG. 1 is an isometric view of one example of a base in accordance with some embodiments.

FIGS. 1-24 illustrate one example of a system in accordance with some embodiments. In some embodiments, system may be used to facilitate a distal metatarsal osteotomy for bunion correction via a minimally invasive surgical (MIS) procedure. Referring first to FIG. 1, a base 100 may include an anchor member 102 that is coupled to an angled body 104 via a pivoting arrangement. In some embodiments, the pivot point 107 about which anchor member 102 and body 104 may pivot is located along an axis defined by hole 106 formed in anchor member 102 and a hole 134 formed through a first component 124 of body 104 as described in greater detail below.

Figure 3:
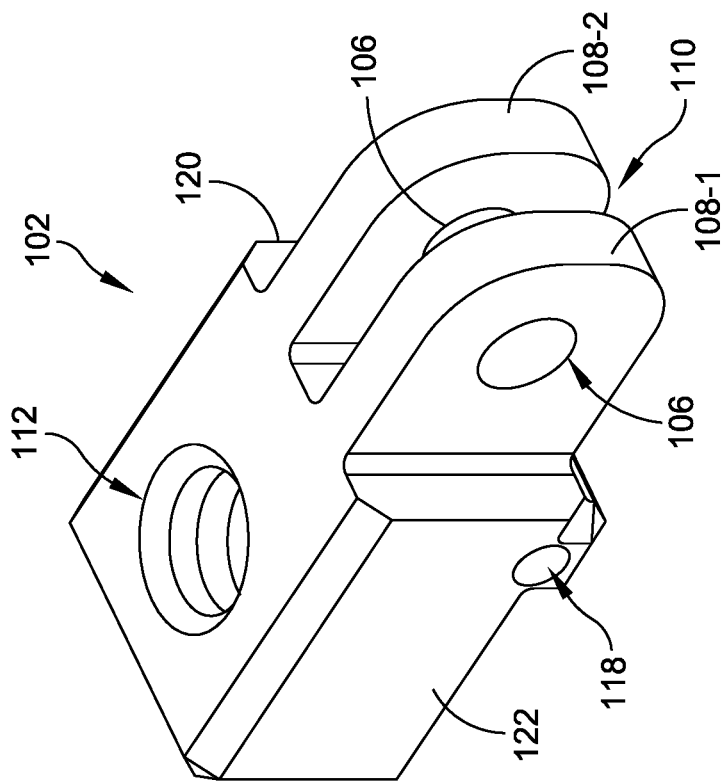
FIG. 3 is a rear side isometric view of the anchor member illustrated in FIG. 2 in accordance with some embodiments.
Figure 2:
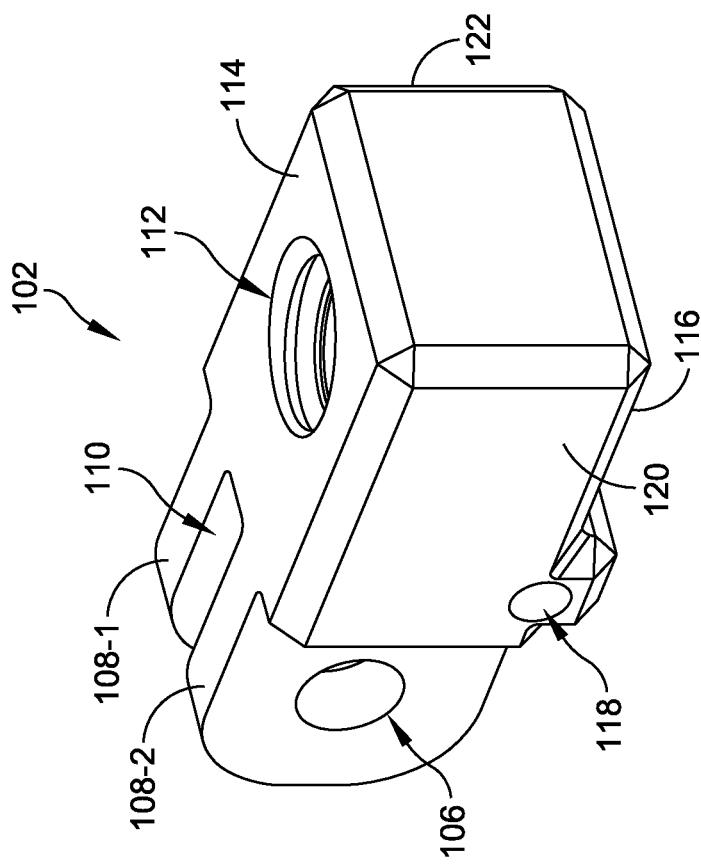
FIG. 2 is a front side isometric view of an anchor member of the base illustrated in FIG. 1 in accordance with some embodiments.
Figure 5:
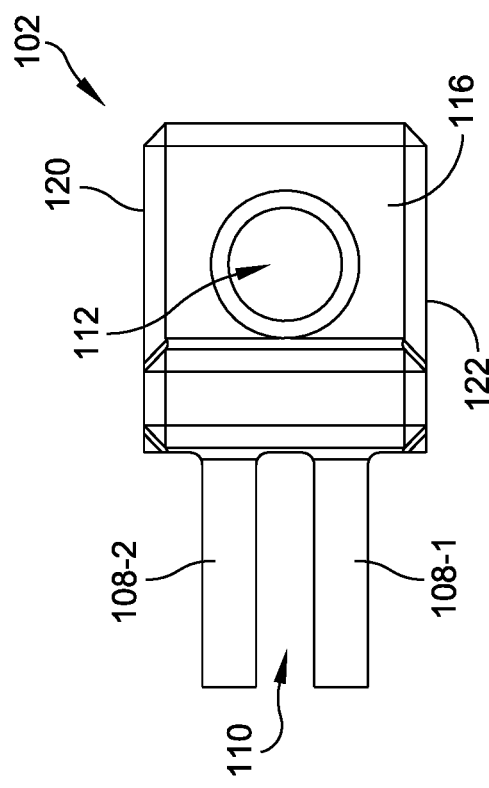
FIG. 5 is a bottom side view of the anchor member illustrated in FIG. 2 in accordance with some embodiments.
Figure 6:
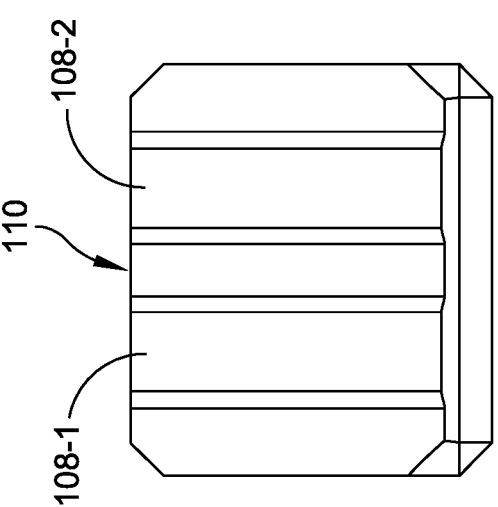
FIG. 6 is a rear side view of the anchor member illustrated in FIG. 2 in accordance with some embodiments.
Figure 4:
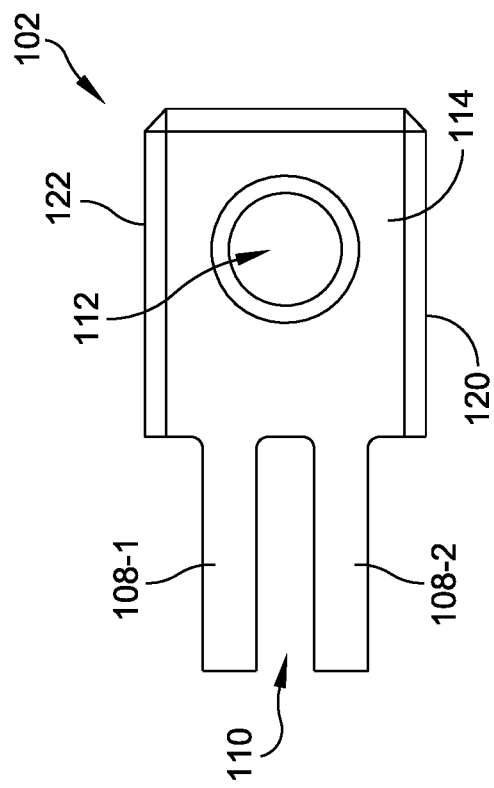
FIG. 4 is a top side view of the anchor member illustrated in FIG. 2 in accordance with some embodiments.

FIGS. 2-6 provide various view of an anchor member 102 in accordance with some embodiments. Referring first to FIGS. 2 and 3, the hole 106 defined by anchor member 102 extends through first and second hinge components 108-1, 108-2 (collectively, "hinge components 108") that are separated from one another by a gap 110.

Anchor member 102 may define a threaded hole 112 extending from a first side 114 to a second side 116. Threaded hole 112 may be sized and configured to engage thumb screw 170 as shown in FIG. 1 and described in greater detail below. Another hole 118 may extend from side 120 through anchor member 102 to side 122. In some embodiments, hole 118 is disposed parallel to hole 106 and perpendicular to hole 112. Holes 106 and 118 may be sized and configured to receive fixation elements, such as a pins or k-wires, for coupling anchor member 102 to a bone or bone segment as described herein.

Figure 7:
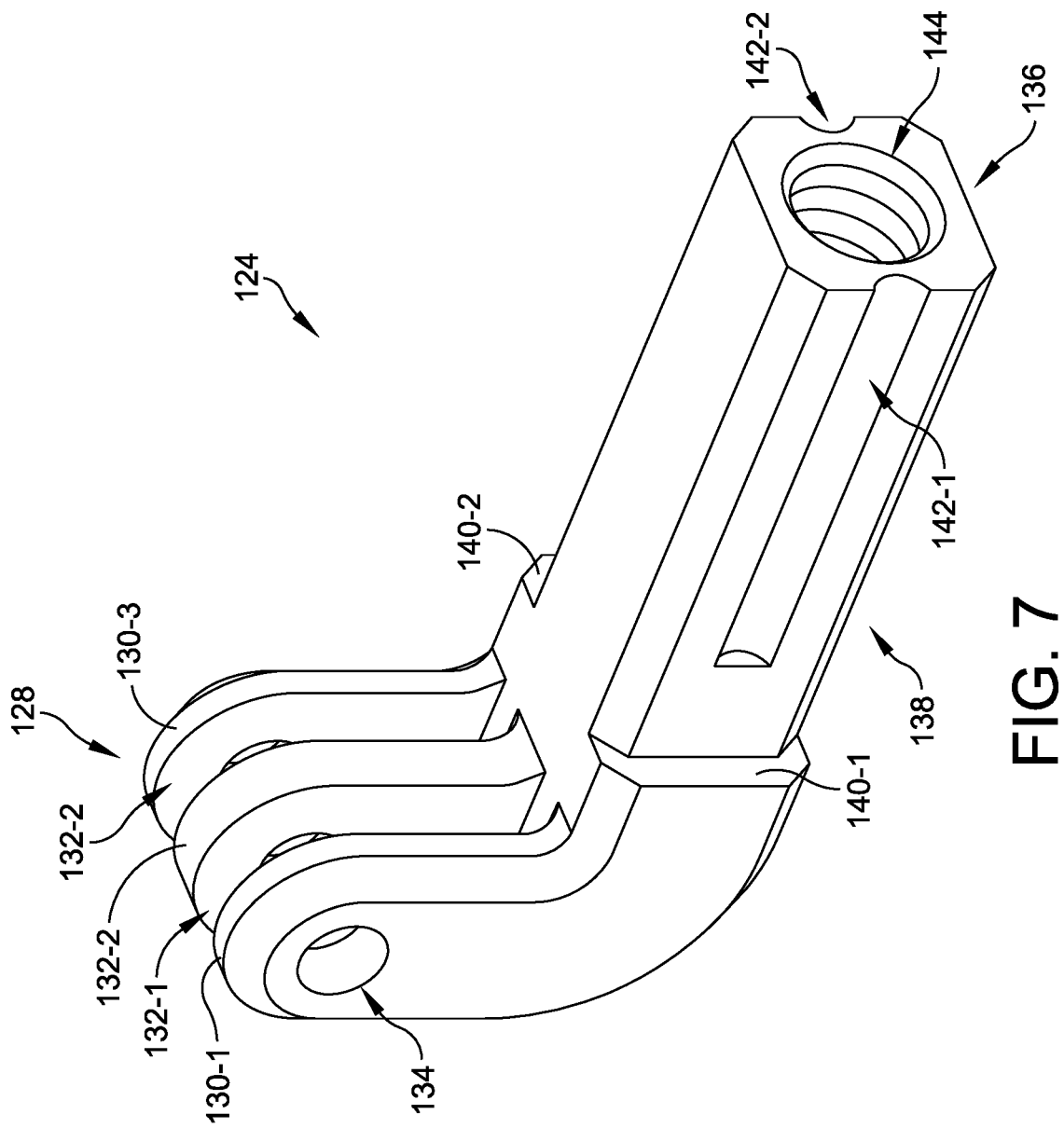
FIG. 7 is a front side isometric view of one component of a body of the base illustrated in FIG. 1 in accordance with some embodiments.
Figure 8:
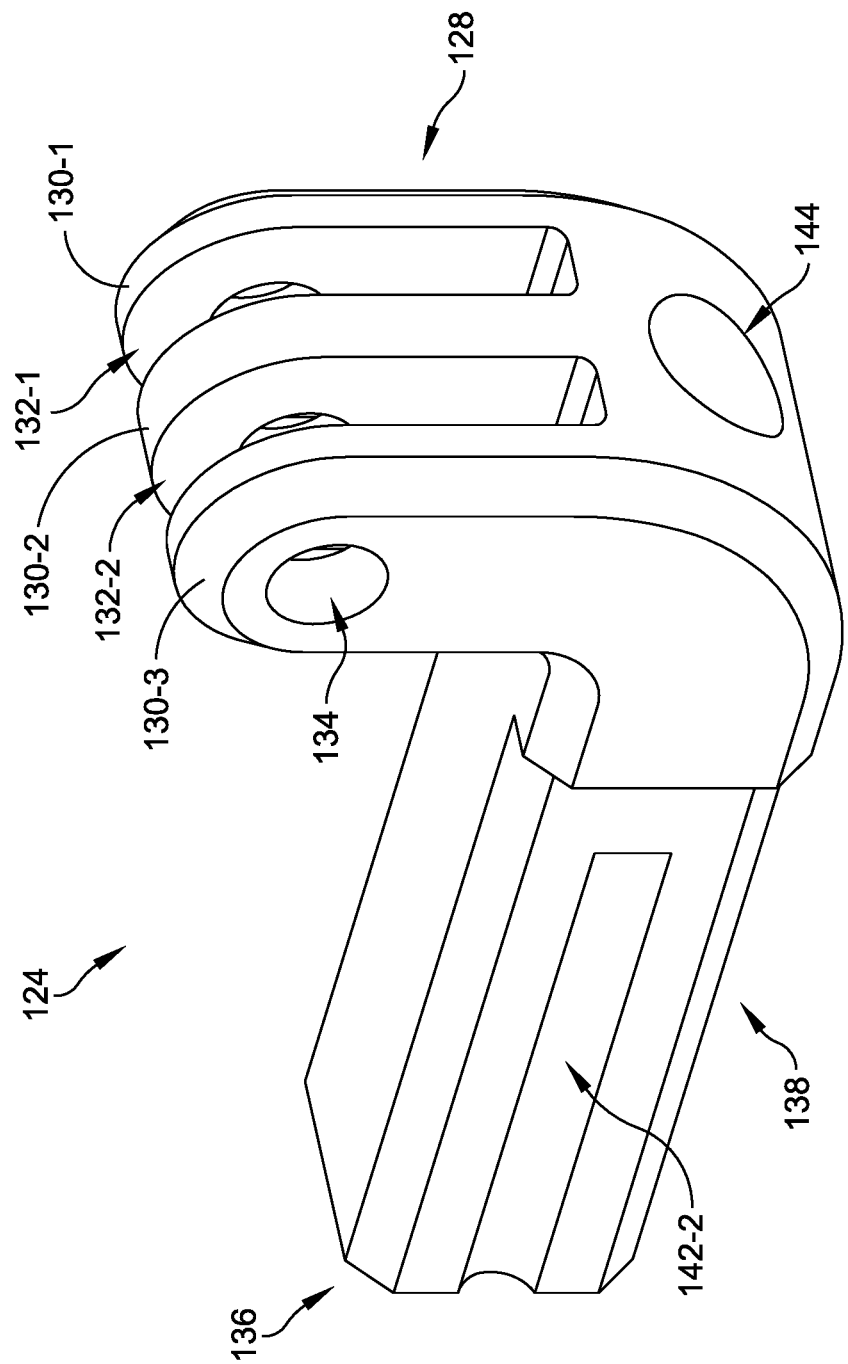
FIG. 8 is a rear side isometric view of the component illustrated in FIG. 7 in accordance with some embodiments.
Figure 10:
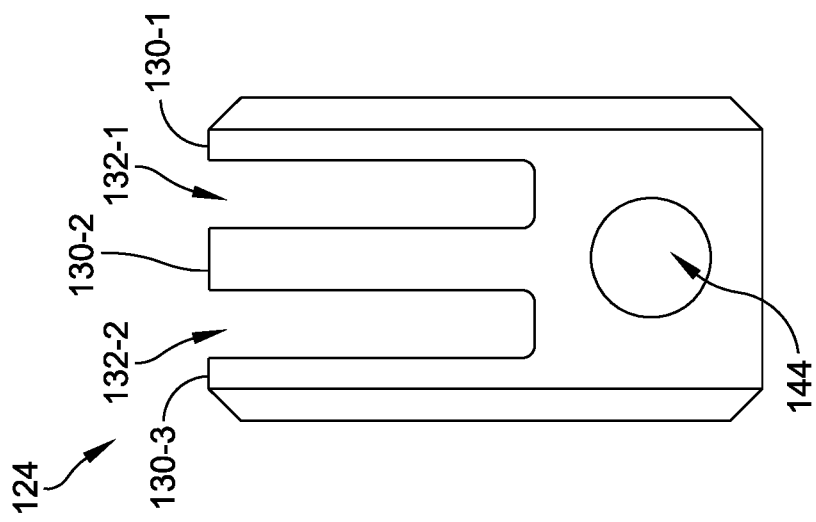
FIG. 10 is a rear side view of the component illustrated in FIG. 7 in accordance with some embodiments.
Figure 9:
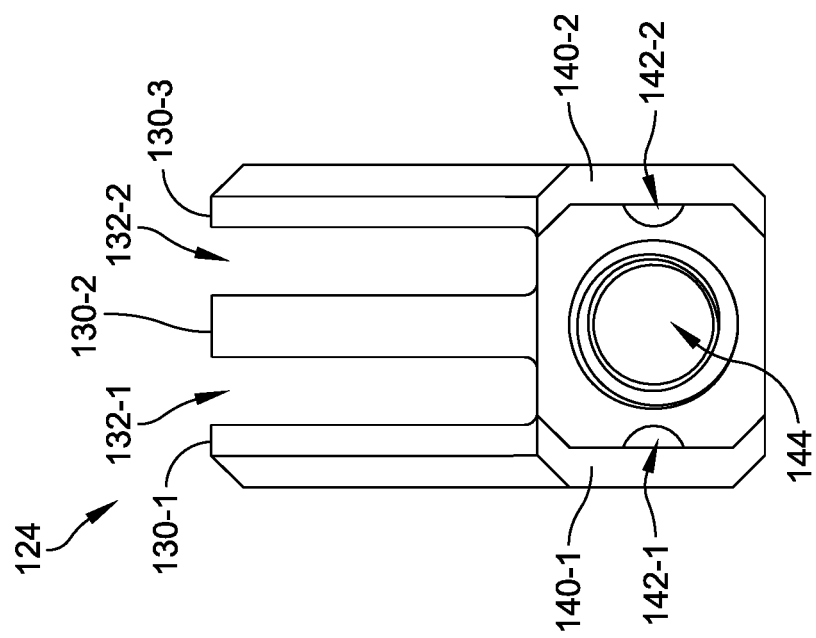
FIG. 9 is a front side view of the component illustrated in FIG. 7 in accordance with some embodiments.
Figure 14:
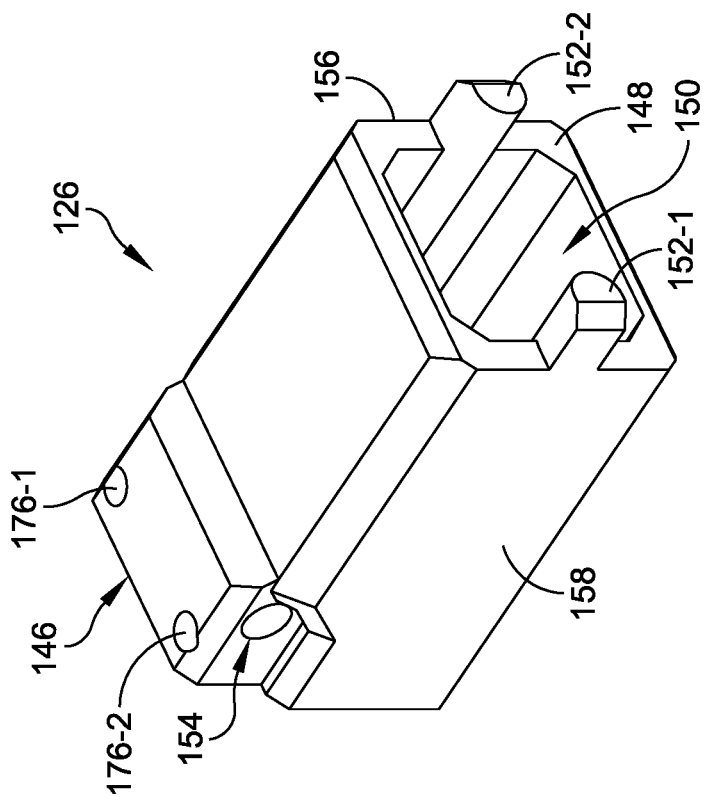
FIG. 14 is a rear side isometric view of the component illustrated in FIG. 13 in accordance with some embodiments.
Figure 13:
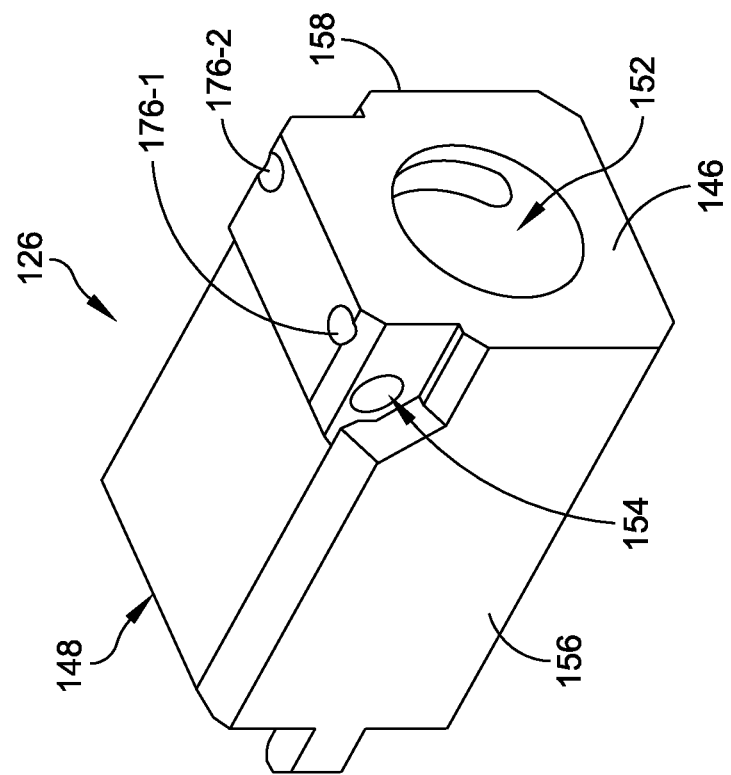
FIG. 13 is a front side isometric view of another component of the body of the base illustrated in FIG. 1 in accordance with some embodiments.

In some embodiments, body 104 includes a first component 124 and a second component 126 that are coupled together such that component 126 may move relative to first component 124. A person of ordinary skill in the art will further understand that, although body 104 is described as including multiple components, body 104 may be provided as a unitary member. As shown in FIG. 7, which is an isometric view of component 124 of body 104, one end 128 of component 124 includes one or more hinge components 130-1, 130-2, 130-3 (collectively, "hinge components 130") that are configured to engage hinge components 108 of anchor member 102. For example, hinge components 130 are spaced apart from one another by gaps 132-1, 132-2 (collectively, "gaps 132"). Note that while three hinge components 130 and two gaps 132 are shown in FIG. 7 fewer or more hinge components 130 and gaps 132 may be provided. Each of the hinge components 130 defines a hole 134 that is sized and configured to receive a fixation element, such as a k-wire or pin, for coupling the body 104 to a bone or bone segment. In some embodiments, hinge components 130 extend at an angle away from a longitudinal axis defined by component 124 between end 128 and end 136.

Component 124 may include a portion 138 having a reduced size (e.g., width) such that one or more shoulders 140-1, 140-2 (collectively, "shoulders 140") are provided adjacent to end 128. One or more channels 142-1, 142-2 (collectively, "channels 142") extend from end 136 towards end 128 along the portion 138. Component 124 may also define a hole 144, which may be at least partially threaded, that extends through component 124 from end 128 to end 136.

One example of the second component 126 is illustrated in FIGS. 13-16. Component 126 extend from a first side 146 to a second side 148 and is substantially hollow. For example, side 148 defines an opening 150 that extends inwardly into component 126 (FIG. 14), and side 148 defines a hole 152 (FIG. 13) that is in communication with opening 150. Opening 150 may extend to a depth such that a majority of the length of the first component 124, or at least a substantial portion of the reduced size portion 138 of component 124, may be received within opening 150.

One or more protrusions 152-1, 152-2 (collectively, "protrusions 152") may extending inwardly into opening 150. Protrusions 152 are sized and configured to align with and be received within channels 142 that extend along component 124. Although protrusions 152 are shown as being part of component 126 and channels are shown as being defined by component 124, one of ordinary skill in the art will understand that the configuration could be reversed and/or each component 124, 126 could include a combination of a protrusion and a channel. Furthermore, in some embodiments, components 124 and 126 may be configured to rotate relative to one another. For example, component 126 may be configured to rotate about the longitudinal axis of component 124 or provide for relative positioning of components 124 and 126 that may enable a bone (or bone segment), such as a first metatarsal, coupled to one of the components (e.g., component 126) to be rotated about a longitudinal axis of the bone.

Component 126 also may define one or more holes 154 that extend laterally through the component. More particularly, the one or more holes 154 may be disposed adjacent to side 148 and extend from side 156 to side 158. Hole 154 is sized and configured to receive a fixation element, such as a k-wire or pin, for securing the component 126 to a bone or bone segment.

Figure 17:
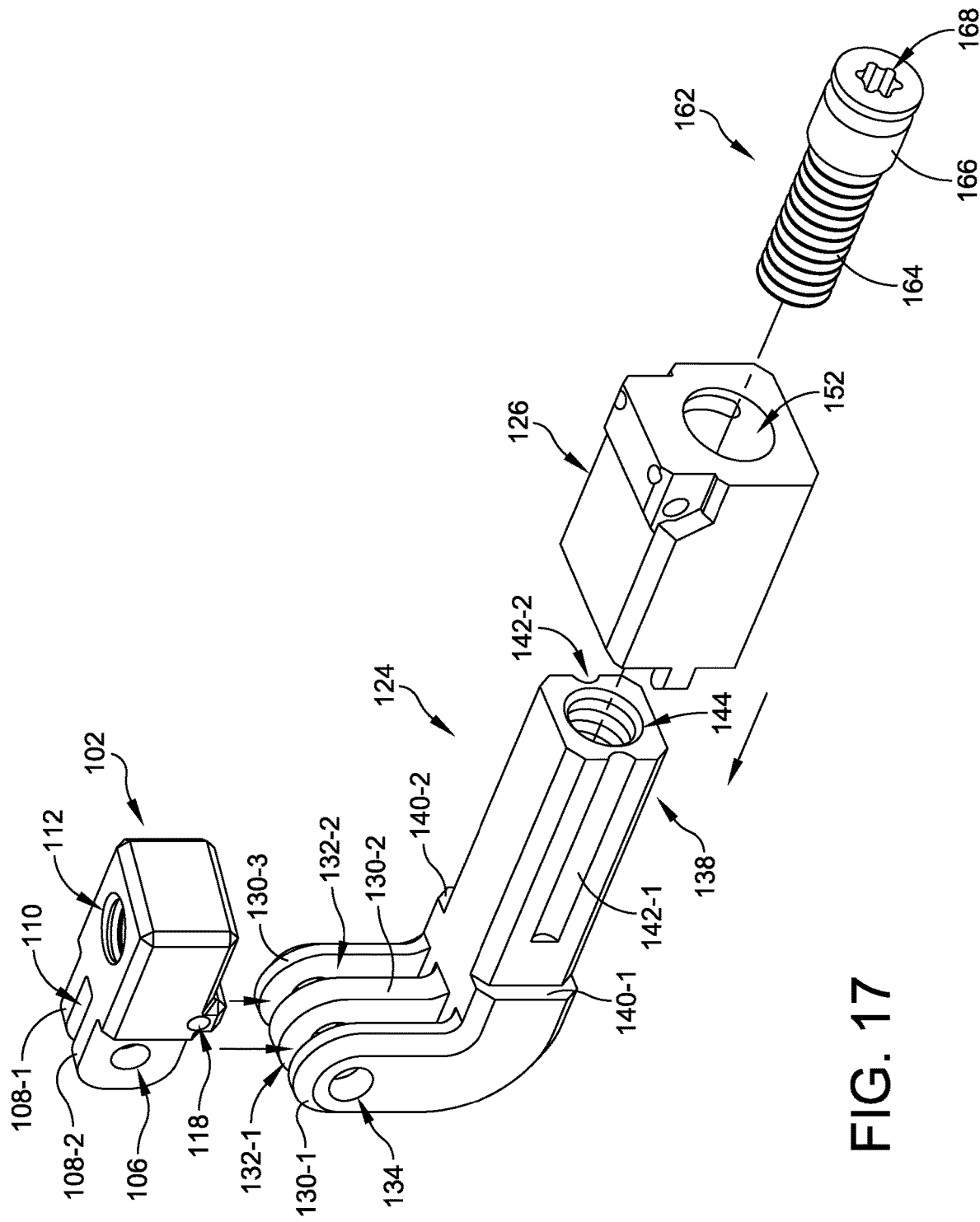
FIG. 17 is an exploded view of the base illustrated in FIG. 1 in accordance with some embodiments.

FIG. 17 illustrates how the anchor member 102 may be coupled to the component 124 of the angled body 104 and how component 126 is coupled to component 124 of angled body. The hinge elements 108 of anchor member 102 are aligned with the gaps 132 between the hinge elements 130 of body 104. The holes 106, 134 defined by the hinge elements 108 of anchor member 102 and defined by the hinge elements 130 of body 104 are then aligned with one another and a coupling element, such as a spring pin 160 (best seen in FIG. 18), is inserted through the aligned holes.

The body components 124 and 126 of body 104 are coupled together by respectively aligning the opening 150 and protrusions of component 126 with the portion 138 and channels 142 of component 124. Once aligned with one another, the component 126 may be slid along the reduced size portion 138 of component 124. An adjustment bolt 162 (shown in FIG. 17, may be received within hole 152 defined by body component 126 and within threaded hole 144 defined by body component 124. Rotation of the adjustment bolt 162 causes relative translation of the first and second components 124, 126. For example, rotation of the adjustment bolt 162 in a first direction (e.g., clockwise) may result in the second component 126 moving along first component 124 and thereby shortening a length of body 104, and rotation of the adjustment bolt 162 in a second direction (e.g., counterclockwise) may result in the second component 126 moving along first component 124 and thereby increasing a length of body 104. As best seen in FIG. 17, the adjustment bolt 162 includes a threaded portion 164 and an enlarged head 166. The head may include an engagement feature 168, which may be configured to receive a driving tool (e.g., a screwdriver, hex key, star driver). In some embodiments, the adjustment bolt may be engaged to component 126 with dowel pins (not shown) that may be received within holes 176-1, 176-2 (collectively, "holes 176") best seen in FIGS. 13-16.

Figure 18:
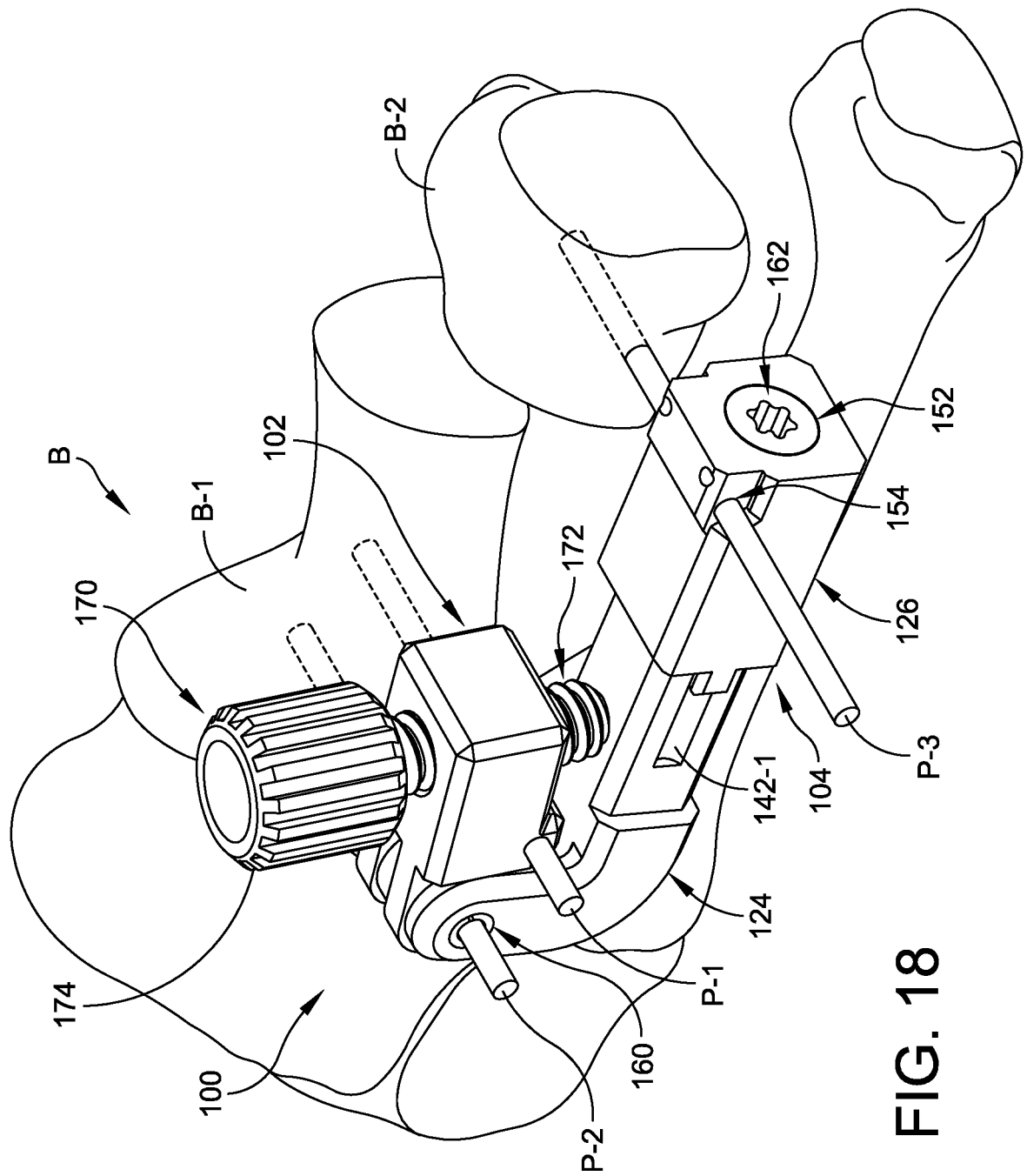
FIG. 18 is an isometric view of the base illustrated in FIG. 1 coupled to bone in accordance with some embodiments.

Referring now to FIG. 18, a thumb screw 170 may be provided for adjusting an angle between anchor member 102 and body 104. Thumb screw 170 includes a threaded portion 172 that is configured to be received within hole 112 defined by anchor member 102. Thumb screw 170 also may include an enlarged head 174 (i.e., has a larger diameter than threaded portion 172) that prevents the head 174 from being received within hole 112 and provides a surgeon with an increased surface area to manipulate the thumb screw 170.

Figure 19:
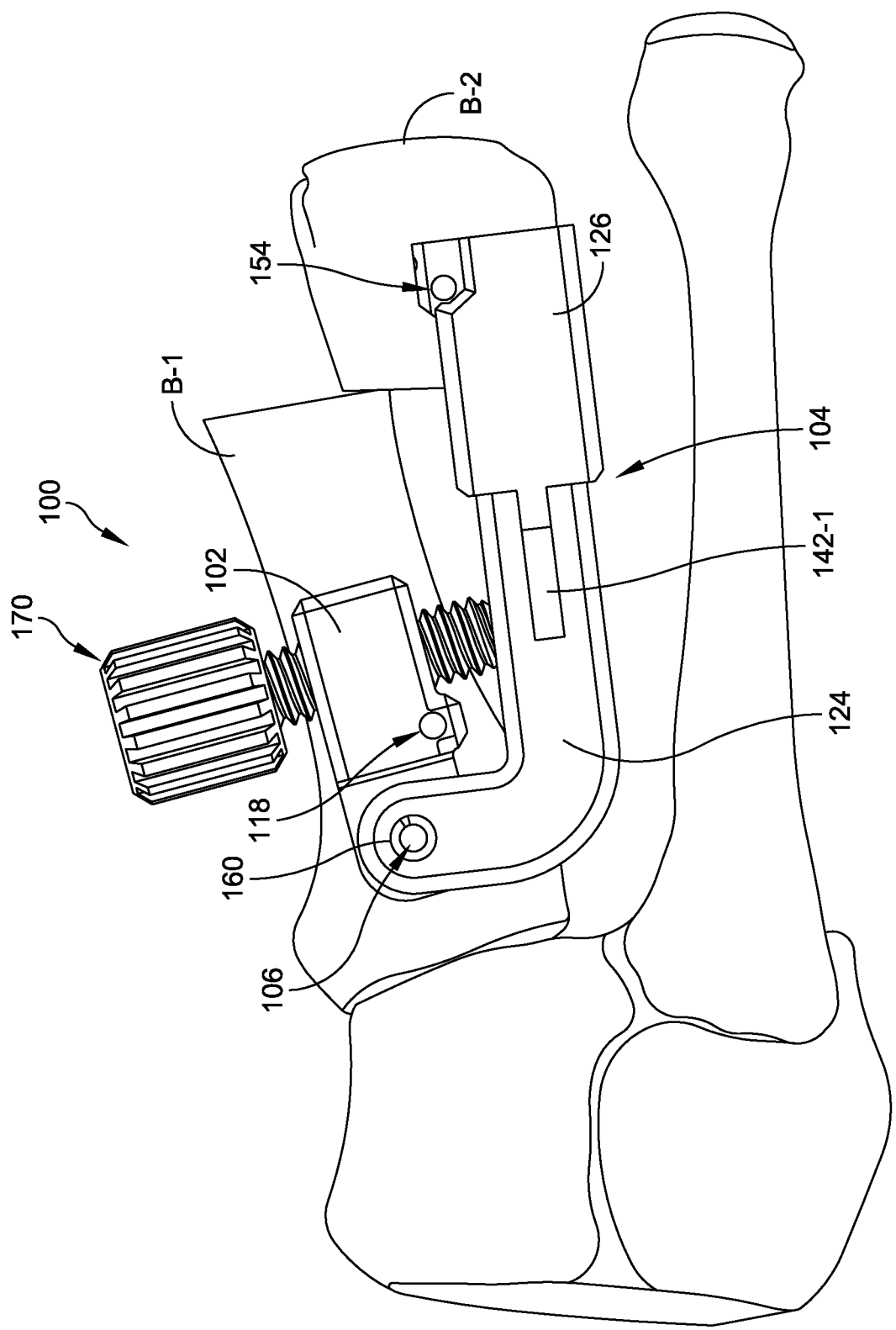
FIG. 19 is a side view of the base illustrated in FIG. 1 coupled to bone in accordance with some embodiments.

Referring to FIGS. 18 and 19, the base 100 is shown coupled to a bone B, which has been cut into two segments B-1, B-2. In some embodiments, the bone B is a metatarsal; however, one of ordinary skill in the art should understand that the disclosed system may be used with other bones. Further, it should be understood that the base 100 may be coupled to the bone B before or after the bone is resected into segments B-1, B-2. Anchor member 102 is coupled to bone B with a first fixation element P-1, e.g., a pin or k-wire, that is inserted through hole 118 defined by anchor member 102.

Another fixation element P-2 couples both the anchor member 102 and body 104 to the bone B. More particularly, fixation element P-2 is inserted through the coupling element 160, which extends between hole 106 defined by anchor member 102 and hole 134 defined by component 124 of body 104. Component 126 of body 104 may be separately coupled to bone B, and more particularly to the bone segment B-2 that may be a metatarsal head, by inserting a fixation element P-3 through lateral hole 154.

As noted above, the base 100 may be coupled to the bone B before or after the bone is segmented into one or more segments B-1, B-2. Regardless of when the base 100 is coupled to the bone, the base 100 may be used to adjust the alignment of the segments B-1 and B-2 relative to one another. For example, thumb screw 170 may be used to move bone segment B-2 (e.g., a severed distal metatarsal head) medially or laterally with respect to the remainder of the metatarsal by rotating the thumb screw 170. Rotating the thumb screw 170 in a first direction (e.g., clockwise) may cause the thumb screw 170 to be advanced into hole 112 defined by anchor member 102, which in turn causes thumb screw 170 to press against body 104 such that body 104 pivots about pivot point 106.

In embodiments in which body 104 includes plural components, adjustment bolt 162 may be used to adjust the position of the bone segment B-2 (e.g., severed distal metatarsal head) along the longitudinal axis defined by body 104. For example, the adjustment bolt 162 may be rotated in a first direction (e.g., clockwise) to cause the second component 126 to move along first component 124 and shorten length of body 104, which in turn will move the bone segment B-2 coupled to the second component 126 proximally towards the rest of the bone B-1 (e.g., a metatarsal). Rotation of the adjustment bolt 162 in a second direction (e.g., counterclockwise) may cause the second component 126 to move along first component 124 in the opposite direction to increasing a length of body 104 and move the bone segment B-2 distally.

Figure 20:
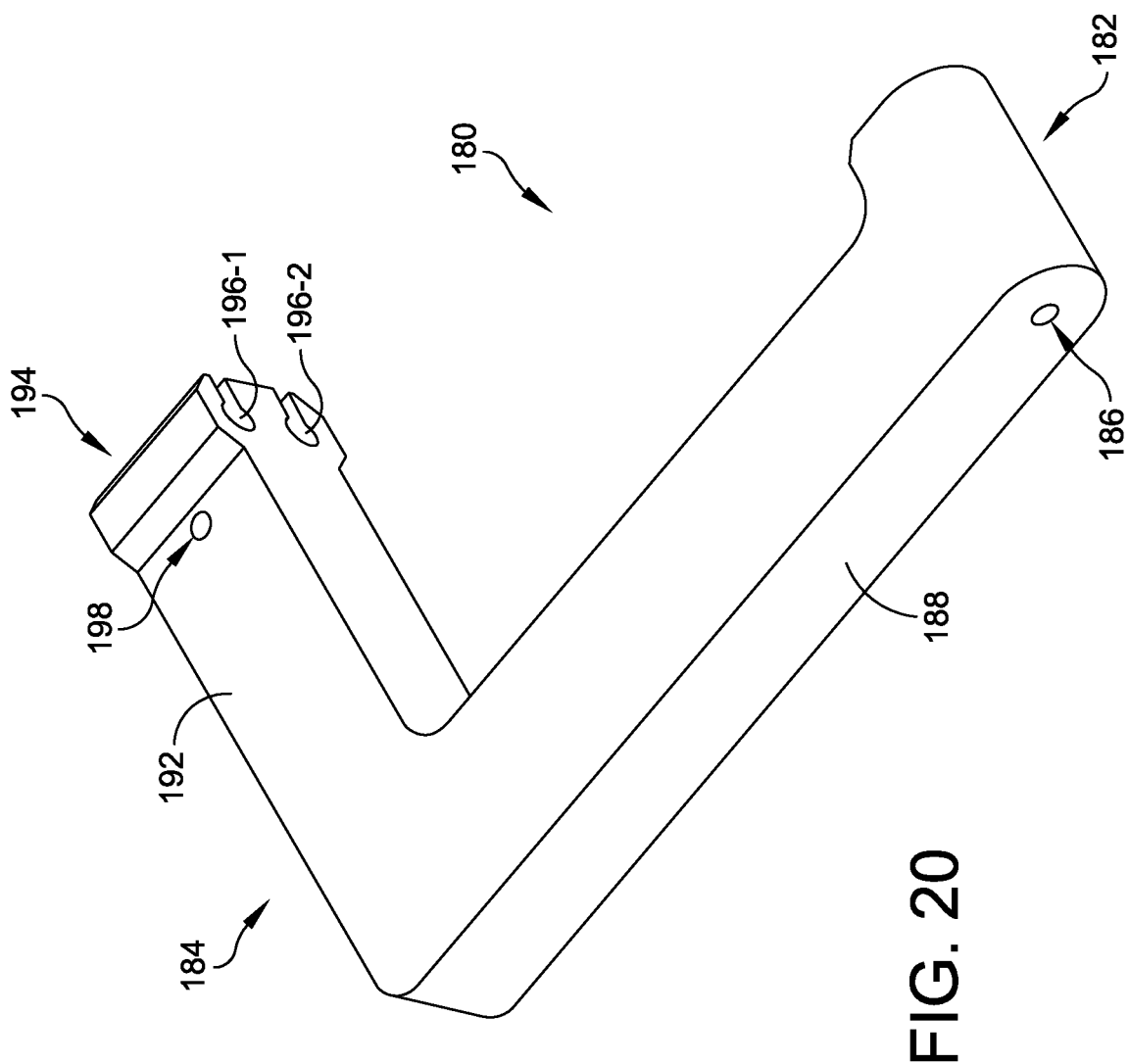
FIG. 20 is an isometric view of one example of a targeting guide in accordance with some embodiments.
Figure 21:
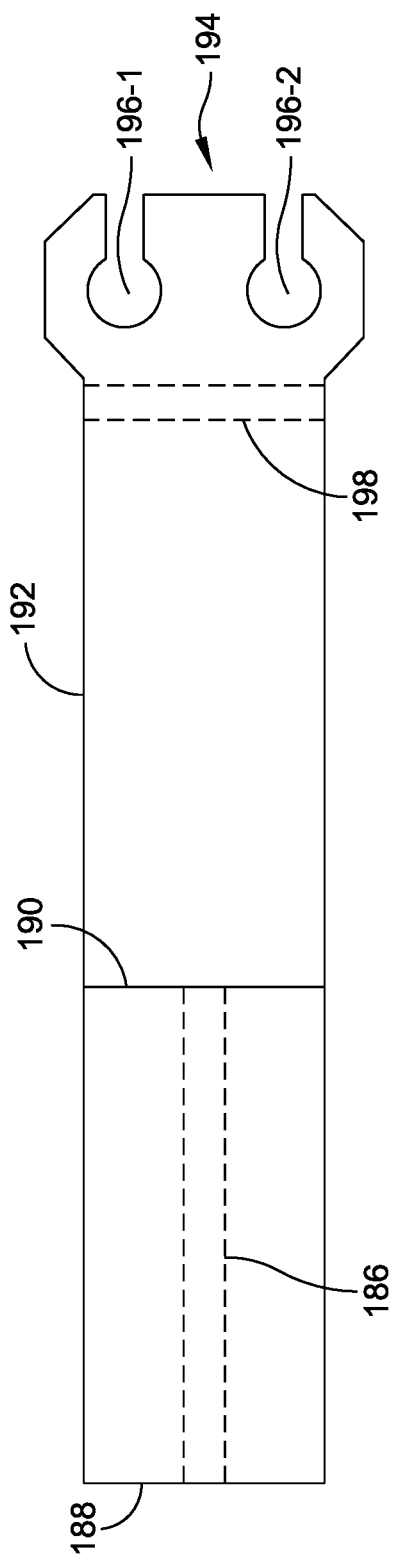
FIG. 21 is a top side view of the targeting guide illustrated in FIG. 20 in accordance with some embodiments.
Figure 22:
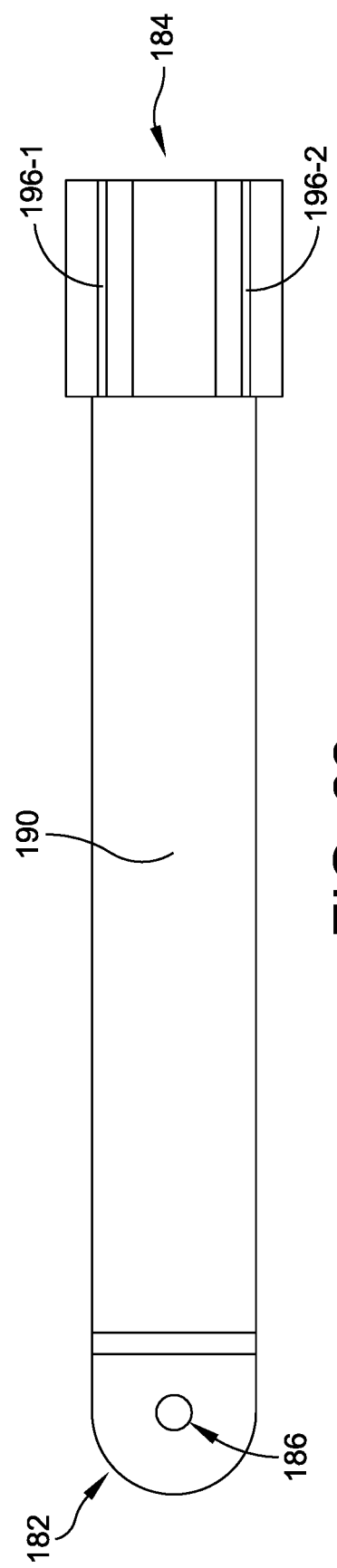
FIG. 22 is a bottom side view of the targeting guide illustrated in FIG. 20 in accordance with some embodiments.
Figure 23:
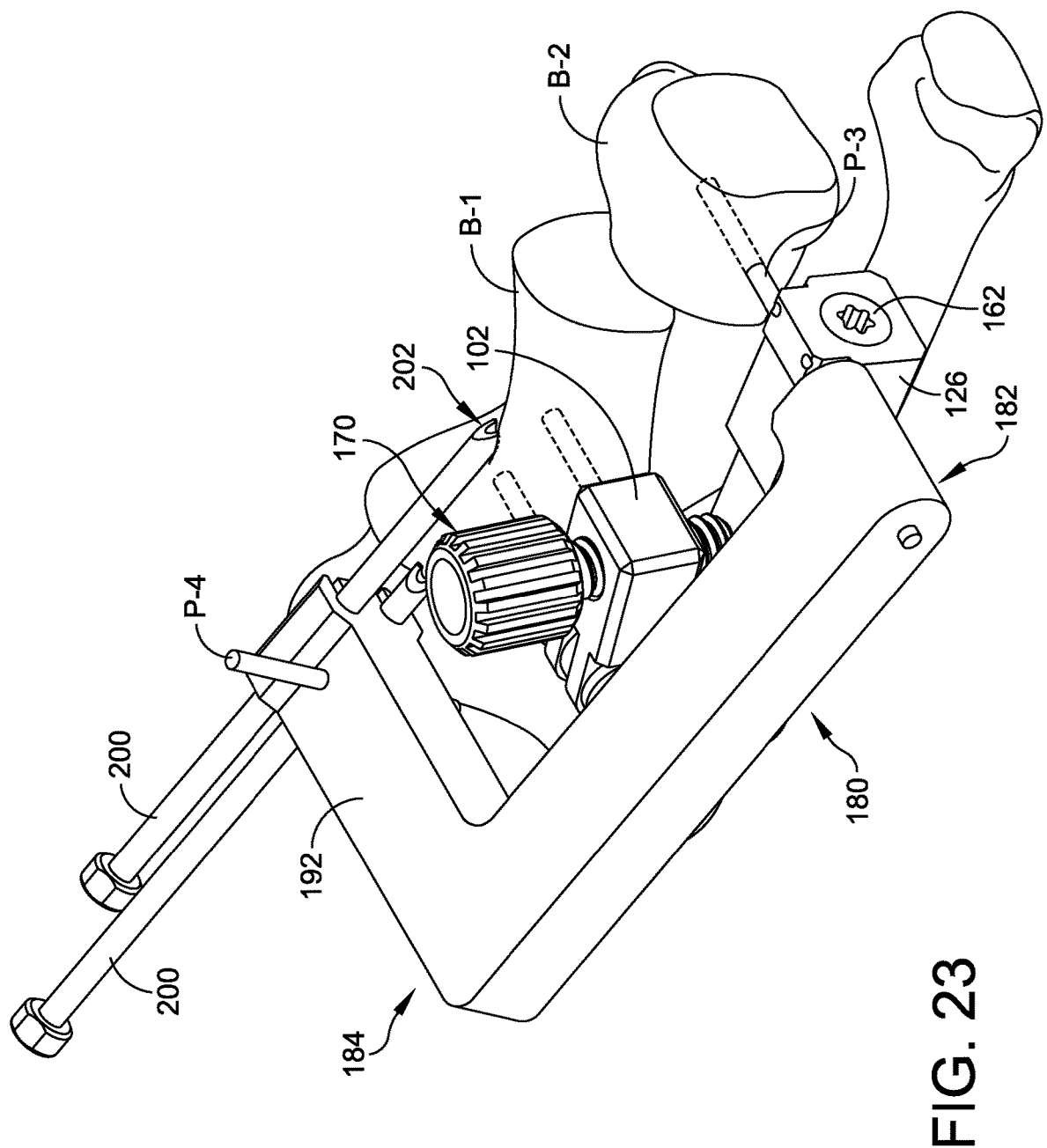
FIG. 23 is an isometric view of the targeting guide illustrated in FIG. 20 coupled to the base illustrated in FIG. 18 in accordance with some embodiments.
Figure 24:
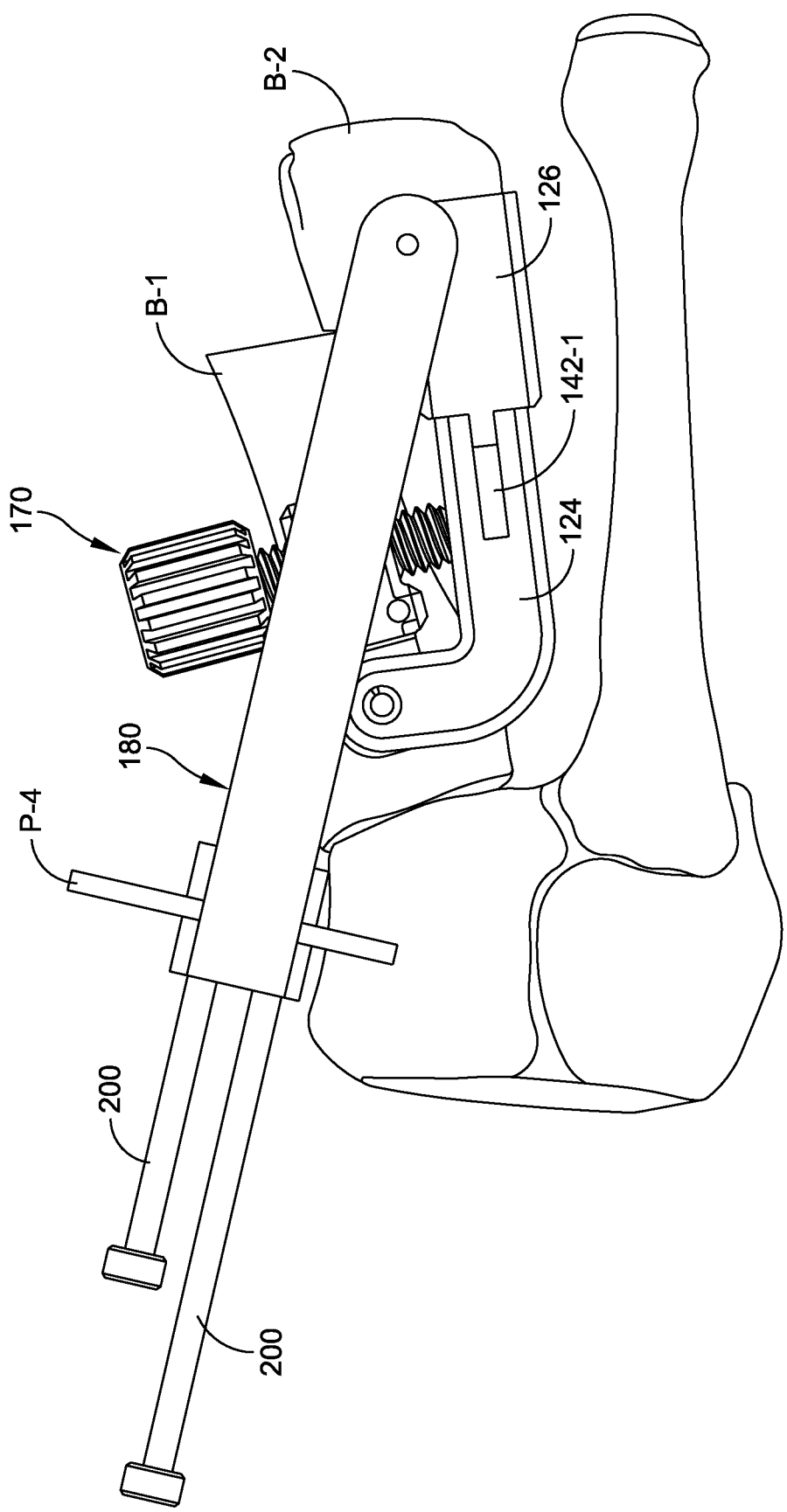
FIG. 24 is a side view of the system illustrated in FIG. 23 in accordance with some embodiments

The base 100 may be used with a targeting device, such as targeting device 180 show in FIGS. 20-22. Note that while targeting device (or guide) 180 is shown as being removably coupled to base, the targeting guide 180 and base 100 may be permanently coupled to one another such that they form a unitary construct. Targeting device 180 includes a first end 182, which may also be referred to as a coupling end, and a second end 184, which may also be referred to a targeting end. Coupling end 182 defines a hole 186 extending from an upper surface 188 to a lower surface 190. Hole 186 is sized and configured to receive a fixation device, such the same k-wire or pin P-3 that is received within hole 154 defined by the second component 126 of body 104.

Targeting end 184 includes an extension 192 that extends in a direction away from the axis of targeting guide 180 that extends from coupling end 182 to the targeting end 184. For example, extension 192 may extend in a direction that is parallel to an axis defined by hole 186 as shown in FIGS. 20 and 22. The lower portion 194 of extension 192 defines a pair of parallel guide holes or slots 196-1, 196-2 (collectively, "guide holes 196" or "guide slots 196"). The guide holes 196 may be positioned parallel to one another and sized and configured to receive a fixation element, such as a k-wire or pin, or an insert or sleeve 200 (shown in FIGS. 23 and 24). If an insert or sleeve 200 is used, then the insert or sleeve 200 may itself define a hole 202 sized and configured to receive a fixation element.

In some embodiments, extension 192 defines another hole 198 that extends laterally through extension 192 as best seen in FIGS. 20 and 21. Put another way, hole 198 extends at an obliquely or perpendicularly with respect to the guide holes 196. Hole 198 is sized and configured to receive a k-wire or pin therein for securing the targeting guide 180 to a bone as described in greater detail below.

Figure 25:
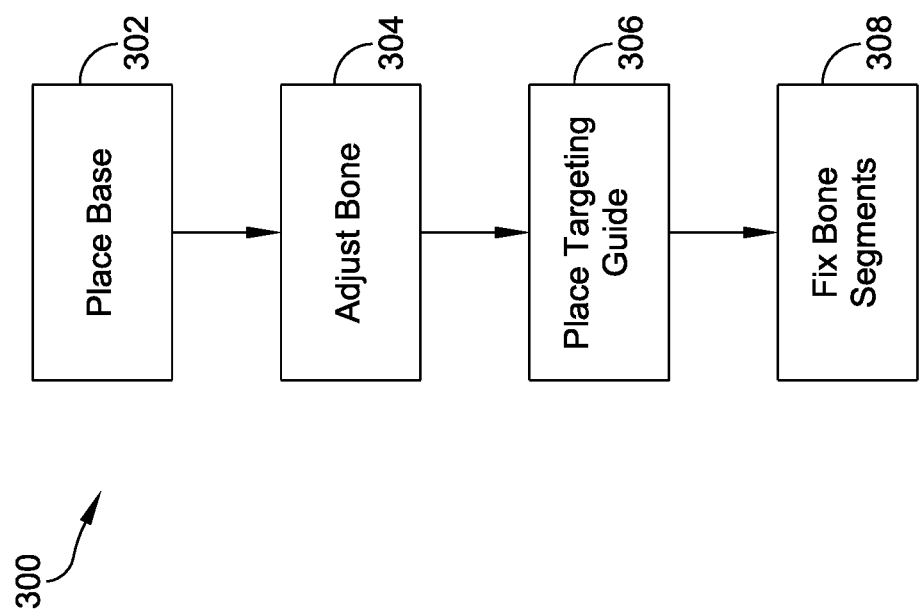
FIG. 25 is one example of a flow diagram of performing a method in accordance with some embodiments.

As noted above, the base 100 and targeting guide 180 may be used as a system for performing a MIS osteotomy for bunion correction or other surgical procedure. FIG. 25 is a flow diagram of one example of a method that may be performed using a base 100 and targeting guide 180 in accordance with some embodiments.

At block 302, the base may be placed. For example, the base 100 may be positioned over a foot such that the hole 154 is located over the distal metatarsal head and holes 106, 134, 118 are positioned over another (e.g., proximal) portion of the same metatarsal. In some embodiments, the base 100 is coupled to the metatarsal by inserting fixation elements (e.g., k-wires or pins) through hole 106, hole 134 and one or more holes 154. The base 100 may be coupled to the metatarsal prior to making a cut through the metatarsal to sever the distal metatarsal head from the rest of the metatarsal. However, one of ordinary skill in the art will appreciate that base 100 may be coupled to the metatarsal and metatarsal head after the metatarsal head is severed.

At block 304, the bone may be adjusted using the base 100. For example, assuming the bone to which the base 100 is coupled has been severed or segmented, the thumbscrew 170 may be used to adjust the relative location of one bone segment B-2 relative to another bone segment B-1. As described above, the rotation of thumbscrew 170 causes the thumb screw 170 to advance into hole 112, which in turn results in the leading end of thumbscrew 170 to press against arm 104 (and, in some embodiments, component 124 of arm 104) thereby pivoting arm 104 about the pivot axis 107 shown in FIG. 1 (and fixation element P-2 shown in FIG. 23).

In embodiments in which body 104 includes multiple components, e.g., components 124, 126, adjustment screw 162 may also be used to adjust the relative location of one bone segment B-2 relative to another bone segment B-1. For example, the adjustment bolt 162 may be rotated in a first direction (e.g., clockwise) to cause the second component 126 to move along first component 124 and shorten length of body 104, which in turn will move the bone segment B-2 coupled to the second component 126 proximally towards the rest of the bone B-1 (e.g., a metatarsal). Rotation of the adjustment bolt 162 in a second direction (e.g., counter-clockwise) may cause the second component 126 to move along first component 124 in the opposite direction to increasing a length of body 104 and move the bone segment B-2 distally.

Further, as discussed above, components 124 and 126 may be configured to rotate relative to one another. For example, component 126 may be configured to rotate about the longitudinal axis of component 124 or provide for relative positioning of components 124 and 126 that may enable a bone (or bone segment), such as a first metatarsal, coupled to one of the components (e.g., component 126) to be rotated about a longitudinal axis of the bone.

Referring again to FIG. 25, the targeting guide 180 is placed into position at block 306. In some embodiments, the targeting guide 180 is placed into position by aligning hole 186 defined by the coupling end 182 of targeting guide 180 with the fixation element P-3 (e.g., pin or k-wire) and then sliding the targeting guide 180 onto the fixation element P-3. With the coupling end 182 of the targeting guide 180 coupled to the fixation element, the targeting end 184 may be moved into its desired position by rotating the targeting guide 180 about the fixation element. Once the desired position of targeting end 184 has been achieved, another fixation element P-4 (e.g., a k-wire or pin) may be inserted through lateral hole 198 and into bone (e.g., the proximal metatarsal portion or another bone) to fix the position of the targeting guide 180.

At 308, the bone segments may be fixed. In some embodiments, k-wires may be inserted through the guide holes or slots 196 (or holes 202 through sleeves or inserts 200) and into the metatarsal segments (i.e., the severed metatarsal head and remaining portion of metatarsal) to fix them relative to one another. Fasteners, such as fasteners 680 as described in commonly assigned U.S. patent application Ser. No. 15/756,446, which is incorporated by reference herein in its entirety, may then be inserted over the k-wires to fix the position of the severed metatarsal head relative to the rest of the metatarsal.

Figure 26:
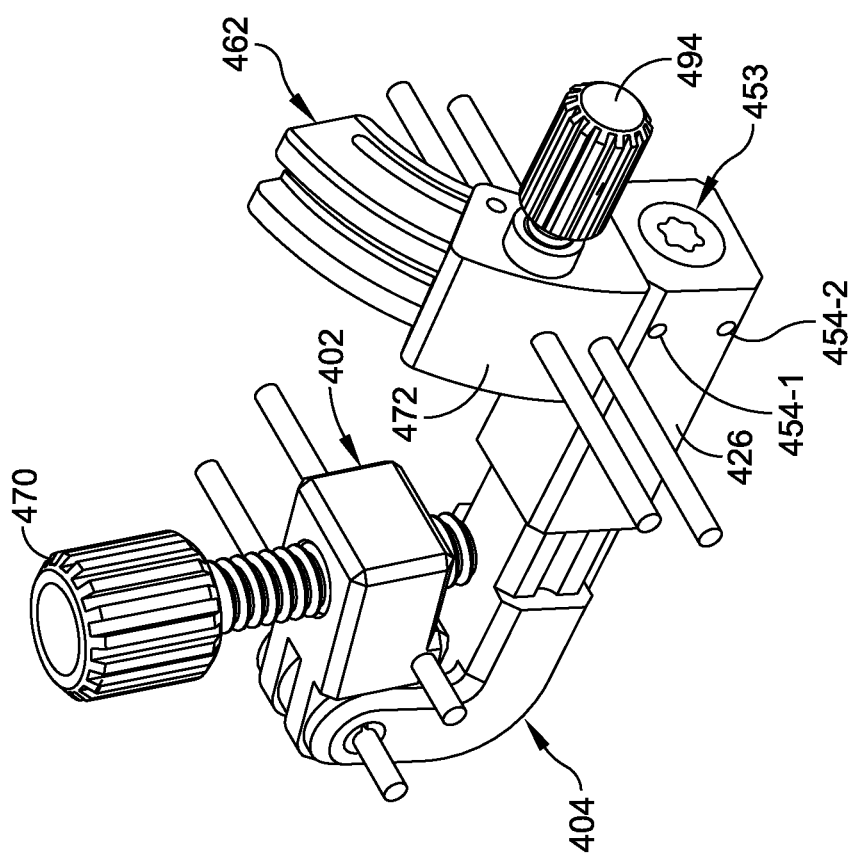
FIG. 26 is an isometric view of another example of a base in accordance with some embodiments.

The method illustrated in FIG. 25 may be used in connection with other systems and devices. For example, FIGS. 26-55 illustrate another example of a system in accordance with some embodiments. Referring first to FIG. 26, a base 400 may include an anchor member 402 that is coupled to an angled body 404 via a pivoting arrangement. In some embodiments, the pivot point about which anchor member 402 and body 404 may pivot is located along an axis defined by hole 406 formed in anchor member 402 and a hole 434 formed through a first component 424 of body 404 as described in greater detail below.

FIGS. 27-31 provide various view of an anchor member 402 in accordance with some embodiments. Referring first to FIGS. 27 and 28, the hole 406 defined by anchor member 402 extends through first and second hinge components 408-1, 408-2 (collectively, "hinge components 408") that are separated from one another by a gap 410.

Anchor member 402 may define a threaded hole 412 extending from a first side 414 to a second side 416. Threaded hole 412 may be sized and configured to engage thumb screw 470 as shown in FIG. 26, which is similar to thumb screw 170 described above and is described in greater detail below. Another hole 418 may extend from side 420 through anchor member 402 to side 422. In some embodiments, hole 418 is disposed parallel to hole 406 and perpendicular to hole 412. Holes 406 and 418 may be sized and configured to receive fixation elements, such as a pins or k-wires, for coupling anchor member 402 to a bone or bone segment as described herein.

Figure 32:
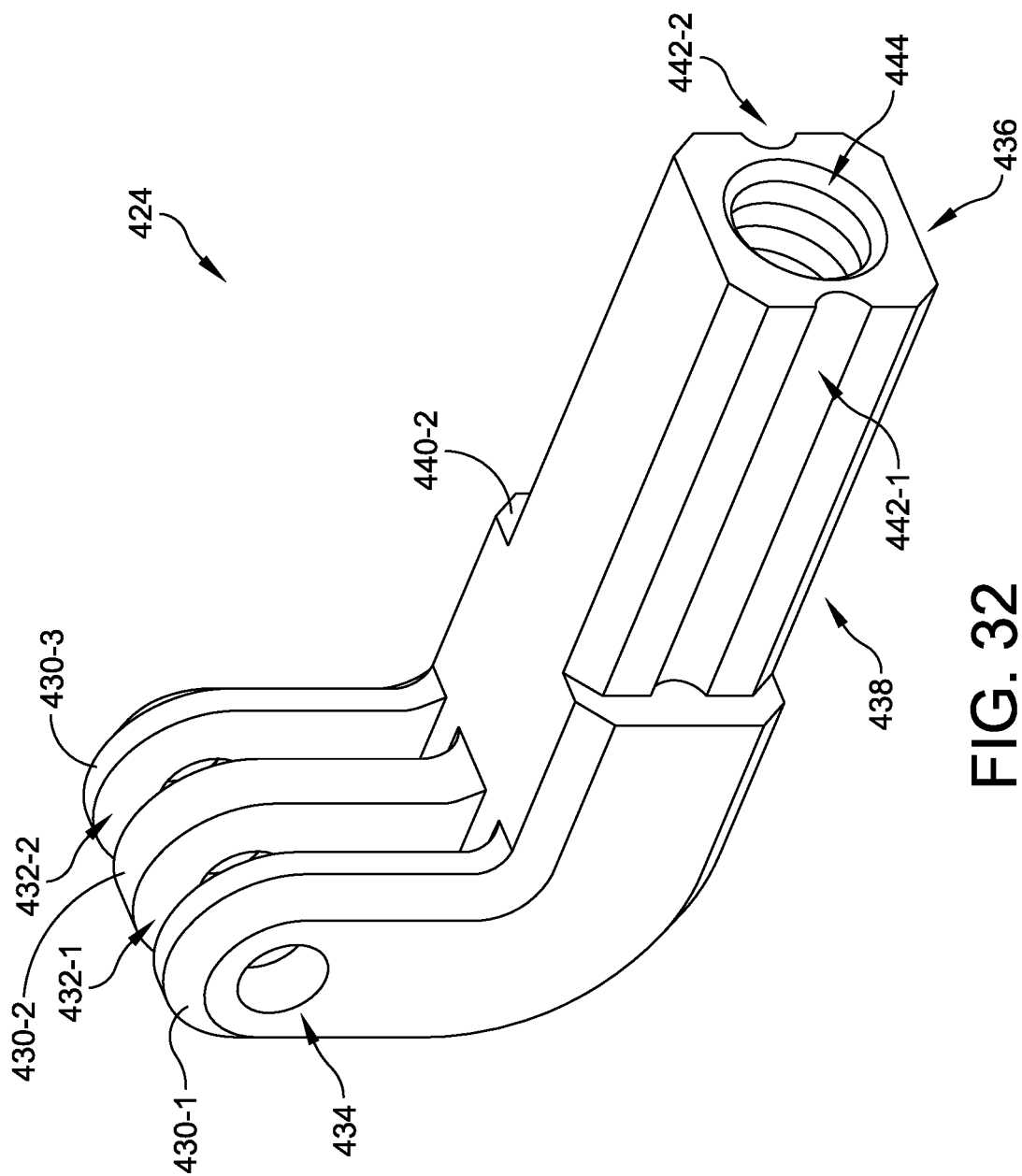
FIG. 32 is a front side isometric view of second component of the base illustrated in FIG. 26 in accordance with some embodiments.
Figure 33:
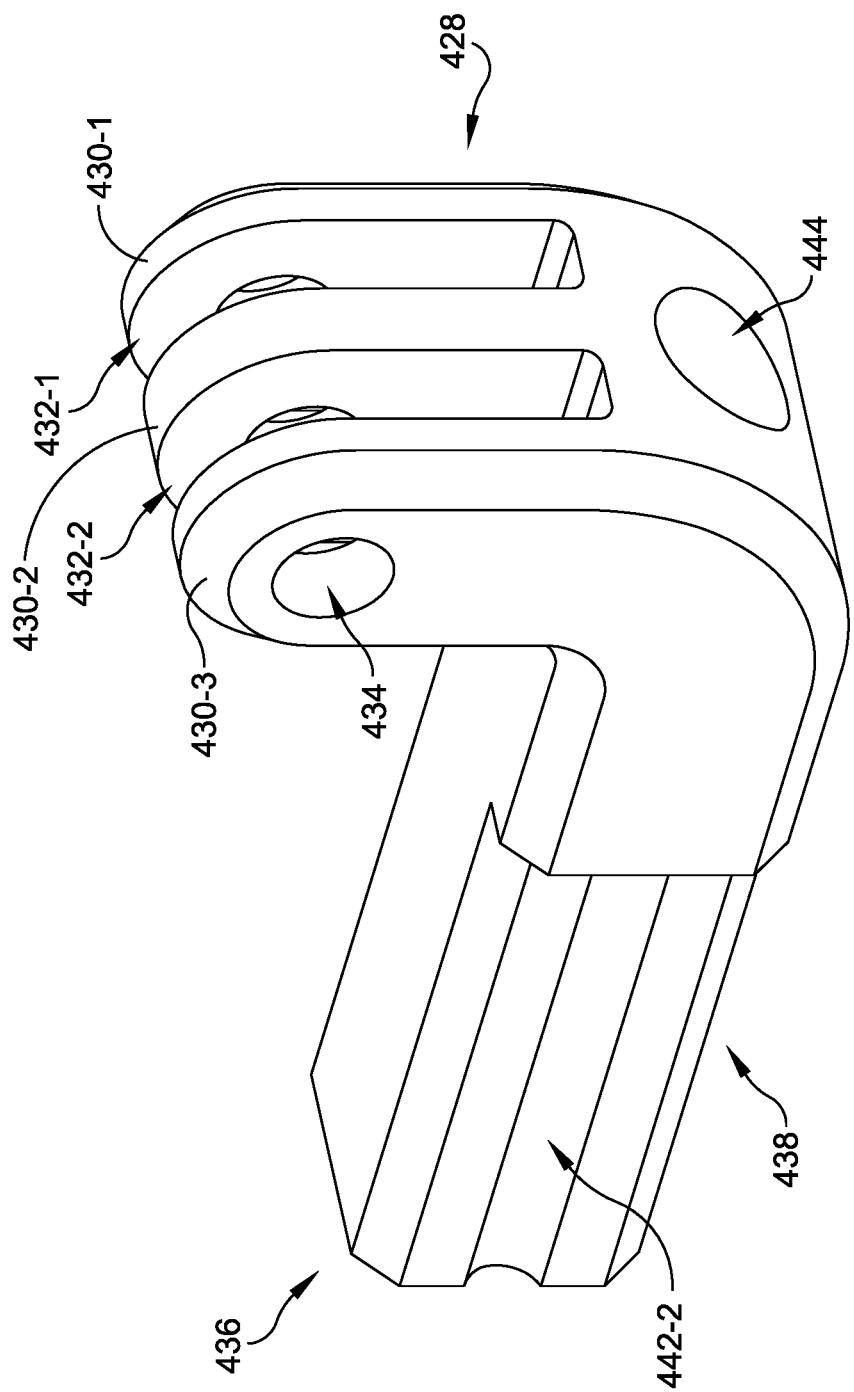
FIG. 33 is a rear side isometric view of the second component illustrated in FIG. 32 in accordance with some embodiments.
Figure 41:
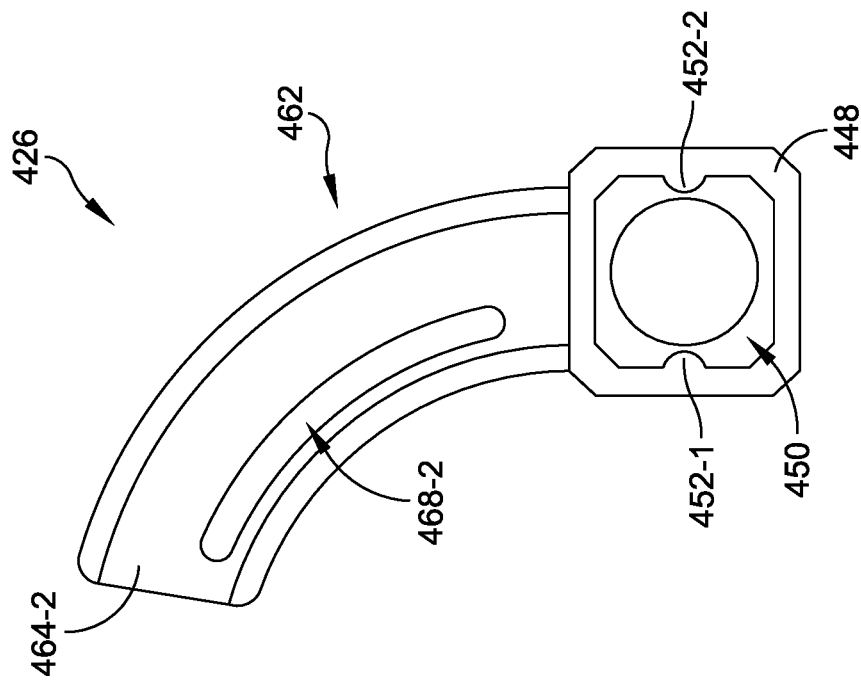
FIG. 41 is a rear side view of the third component illustrated in FIG. 38 in accordance with some embodiments.
Figure 40:
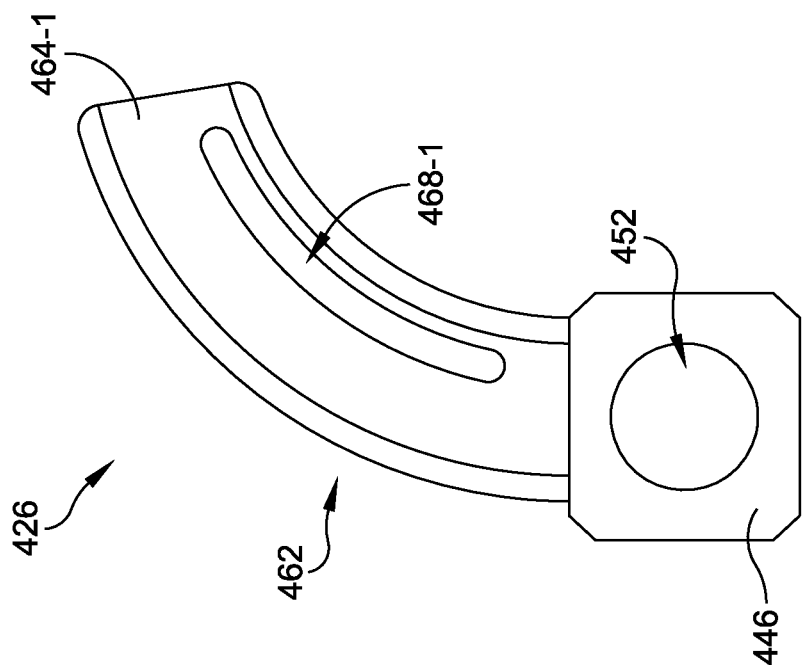
FIG. 40 is a front side view of the third component illustrated in FIG. 38 in accordance with some embodiments.
Figure 46:
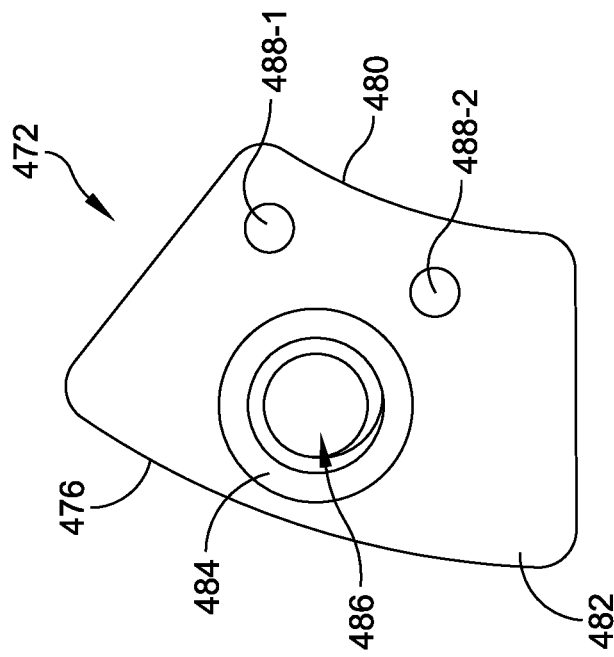
FIG. 46 is a front side view of the fourth component illustrated in FIG. 45 in accordance with some embodiments.
Figure 45:
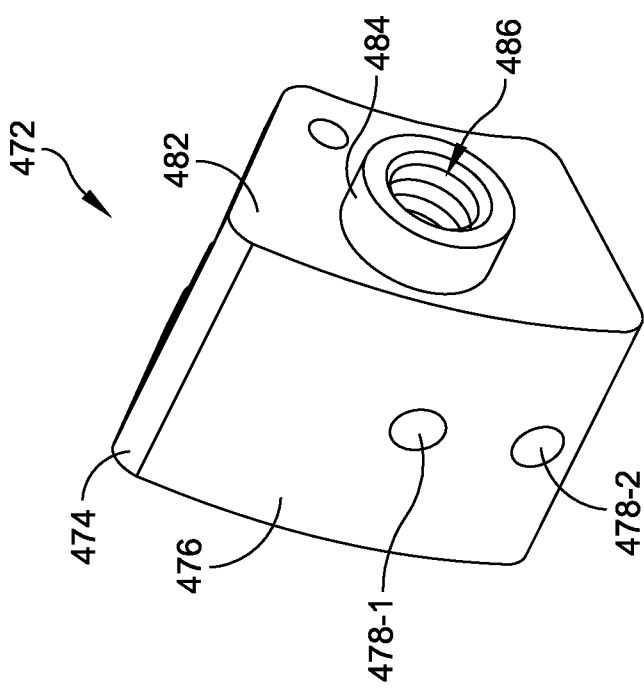
FIG. 45 is a front side isometric view of a fourth component of the base illustrated in FIG. 26 in accordance with some embodiments.

In some embodiments, body 404 includes a first component 424 and a second component 426 that are coupled together such that component 426 may move relative to first component 424. A person of ordinary skill in the art will further understand that, although body 404 is described as including multiple components, body 404 may be provided as a unitary member. As shown in FIG. 32, which is an isometric view of component 424 of body 404, one end 428 of component 424 includes one or more hinge components 430-1, 430-2, 430-3 (collectively, "hinge components 430") that are configured to engage hinge components 408 of anchor member 402. For example, hinge components 430 are spaced apart from one another by gaps 432-1, 432-2 (collectively, "gaps 432"). Note that, while three hinge components 430 and two gaps 432 are shown in FIG. 32, fewer or more hinge components 430 and gaps 432 may be provided without departing from the scope and spirit of the disclosure. Each of the hinge components 430 defines a hole 434 that is sized and configured to receive a fixation element, such as a k-wire or pin, for coupling the body 404 to a bone or bone segment. In some embodiments, hinge components 430 extend at an angle away from a longitudinal axis defined by component 424 between end 428 and end 436.

Component 424 may include a portion 438 having a reduced size (e.g., width) such that one or more shoulders 440-1, 440-2 (collectively, "shoulders 440") are provided adjacent to end 428. One or more channels 442-1, 442-2 (collectively, "channels 442") extend from end 436 towards end 428 along the portion 438. Component 424 may also define a hole 444, which may be at least partially threaded, that extends through component 424 from end 428 to end 436.

One example of the second component 426 is illustrated in FIGS. 38-44. Component 426 extends from a first side 246 to a second side 448 and is substantially hollow. For example, side 448 defines an opening 450 that extends inwardly into component 426 (FIG. 39), and side 448 defines a hole 452 (FIG. 38) that is in communication with opening 450. Opening 450 may extend to a depth such that a majority of the length of the first component 424, or at least a substantial portion of the reduced size portion 438 of component 424, may be received within opening 450. Hole 452 is sized and configured to receive an adjustment bolt 453 therein. Adjustment bolt 453 may be the same or similar as adjustment bolt 162 described above.

One or more protrusions 451-1, 451-2 (collectively, "protrusions 451") may extend inwardly into opening 450. Protrusions 451 are sized and configured to align with and be received within channels 442 that extend along component 424. Although protrusions 451 are shown as being part of component 426 and channels are shown as being defined by component 424, one of ordinary skill in the art will understand that the configuration could be reversed and/or each component 424, 426 could include a combination of a protrusion and a channel.

One or more holes 454-1, 454-2 (collectively, "holes 454") may extend from side 456 to side 458 through component 426 as best seen in FIGS. 38 and 39. Holes may be sized and configured to receive a pin or other coupling device for securing an adjustment bolt 453 to component 426.

In some embodiments, component 426 includes a curved extension 462 extending from side 460. Extension 462 may include a pair of spaced apart arms 464-1, 464-2 (collectively, "arms 464") that are separated from each other by slot or gap 466 best seen in FIGS. 42-44. Each arm 464-1, 464-2 may define a respective slot 468-1, 468-2 (collectively, "slots 468") that extends through the arm. In some embodiments, the slots 468 have the same curvature as the curvature of the extension 462. However, one of ordinary skill in the art will understand that slots 468 may have other shapes. Slots 468 are sized and configured to receive a dowel, cross-pin or other securement device as described below. Each arm 464 may also include a shelf 470 extending inwardly from the arm (i.e., towards gap 466) as shown in FIGS. 42-44.

FIGS. 45-48 illustrate one example of a mounting component 472 that may be coupled to and supported by the extension 462. Mounting component 472 includes a body 474 that may have a curved shaped similar to the shape of extension 462. One side 476 of component 472 defines one or more holes 478-1, 478-2 (collectively, "holes 478") that extend through body 474 to side 480. Holes 478 may be sized and configured to receive fixation elements (e.g., k-wire or pin) therethrough.

Side 482, which may be positioned between sides 476 and 480, may include an outwardly extending protrusion 484, which defines a hole 486 that extends through body 474. In some embodiments, hole 486 is threaded. Side 482 may also define one or more holes 488-1, 488-2 (collectively, "holes") that extend through body 474. Holes 488 may be sized and configured to receive dowel, cross-pins, or other securement for coupling mounting component 472 to arms 464 of extension 462 via slots 468.

Figure 48:
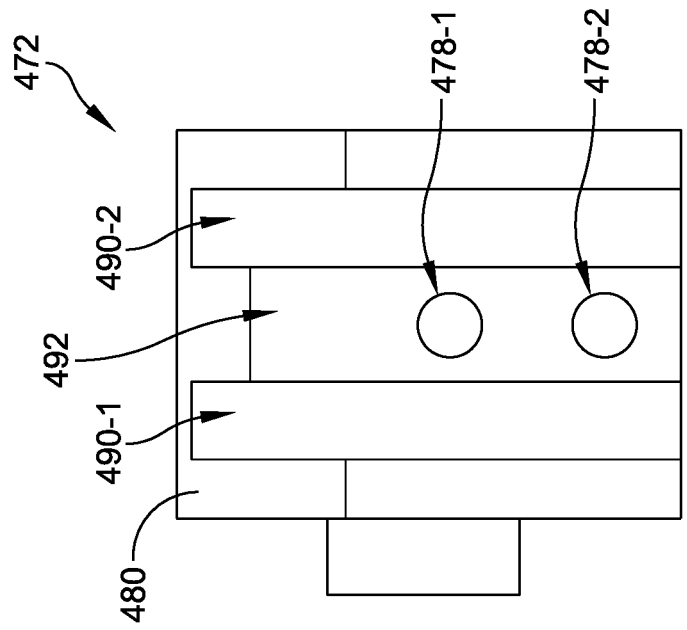
FIG. 48 is aside view opposite of that shown in FIG. 47 of the fourth component illustrated in FIG. 45 in accordance with some embodiments.
Figure 47:
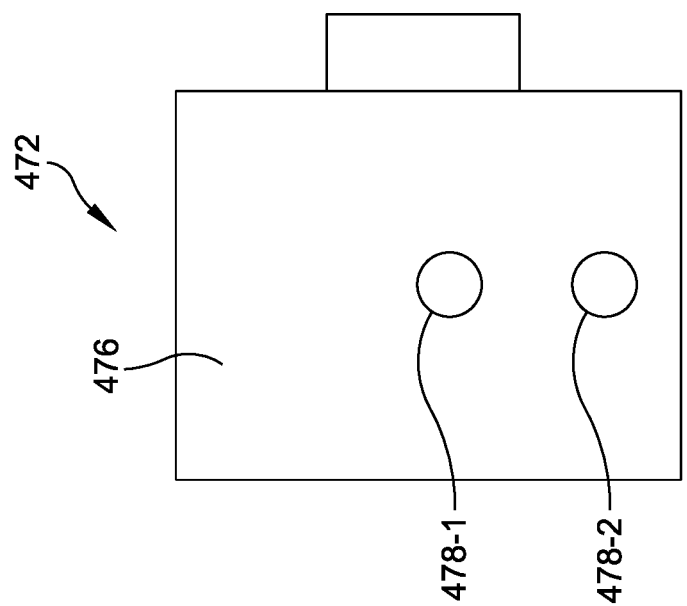
FIG. 47 is a side view of the fourth component illustrated in FIG. 45 in accordance with some embodiments.

As best seen in FIG. 48, side 480 defines a pair of slots 490-1, 490-2 (collectively, "slots 490") that are formed on either side of a guide 492. Slots 490 are positioned and dimensioned to correspond to receive the upper portions of arms 464 therein when guide 492 is received within the gap 466. In some embodiments, guide 492 may contact or abut shelf 470; however, one of ordinary skill in the art will understand that the shelf 470 may provide clearance for guide 492.

Figure 49:
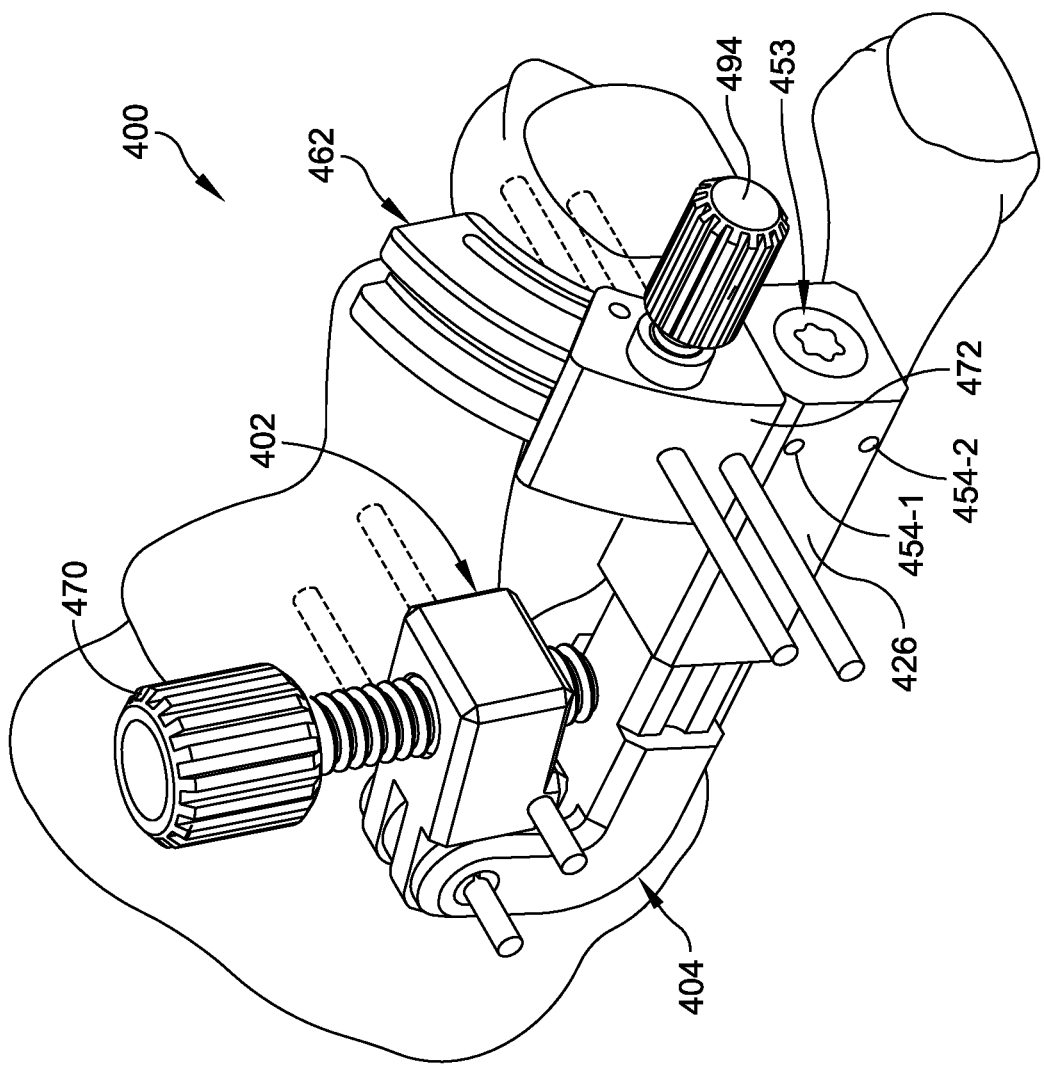
FIG. 49 is an isometric view of the base shown in FIG. 26 being coupled to bone in accordance with some embodiments.

Threaded hole 486 is sized and configured to receive a thumbscrew 494 therein as best seen in FIG. 49. Thumbscrew 494 may be rotated relative to mounting component 472, which results in thumb screw 494 being advanced into or out of hole 486. Advancement of the thumb screw 494 into hole 486 will result in the leading end of thumb screw 484 contacting the extension 462 to secure the location of mounting component 472 along mounting component 472.

Figure 50:
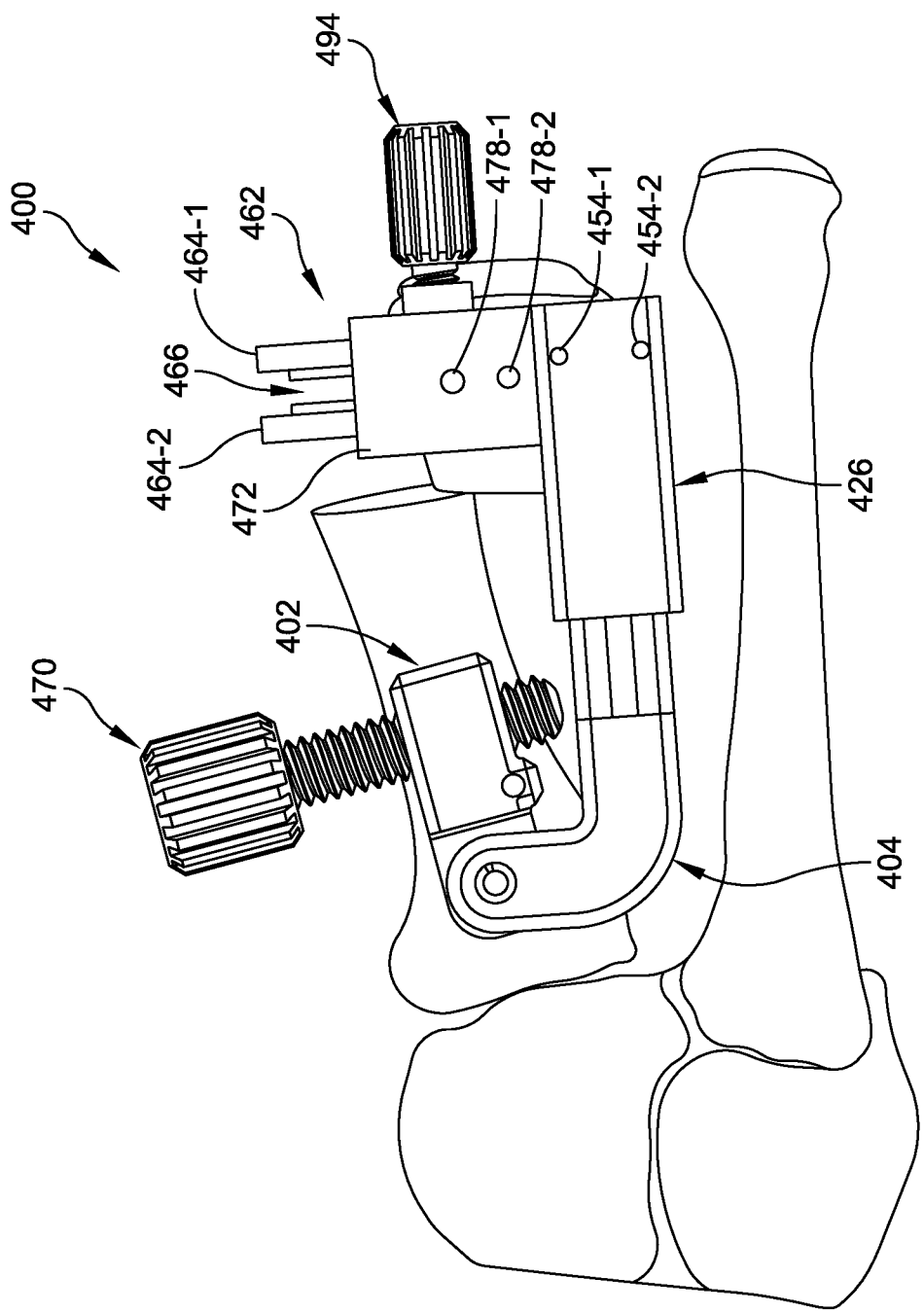
FIG. 50 is a side view of the base shown in FIG. 26 coupled to bone in accordance with some embodiments.
Figure 51:
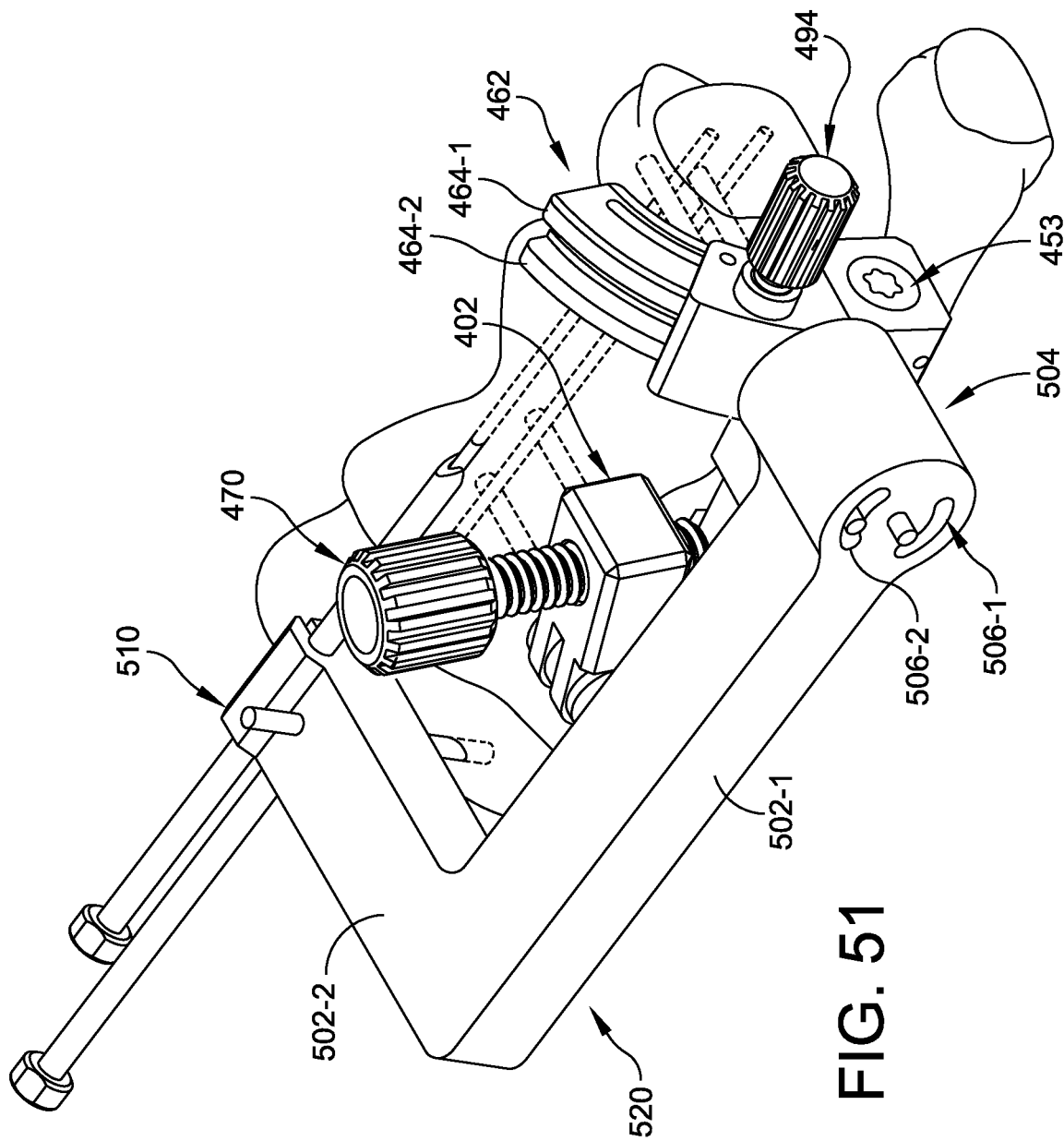
FIG. 51 is an isometric view of the base shown in FIG. 26 and a targeting guide coupled to bone in accordance with some embodiments.
Figure 52A:
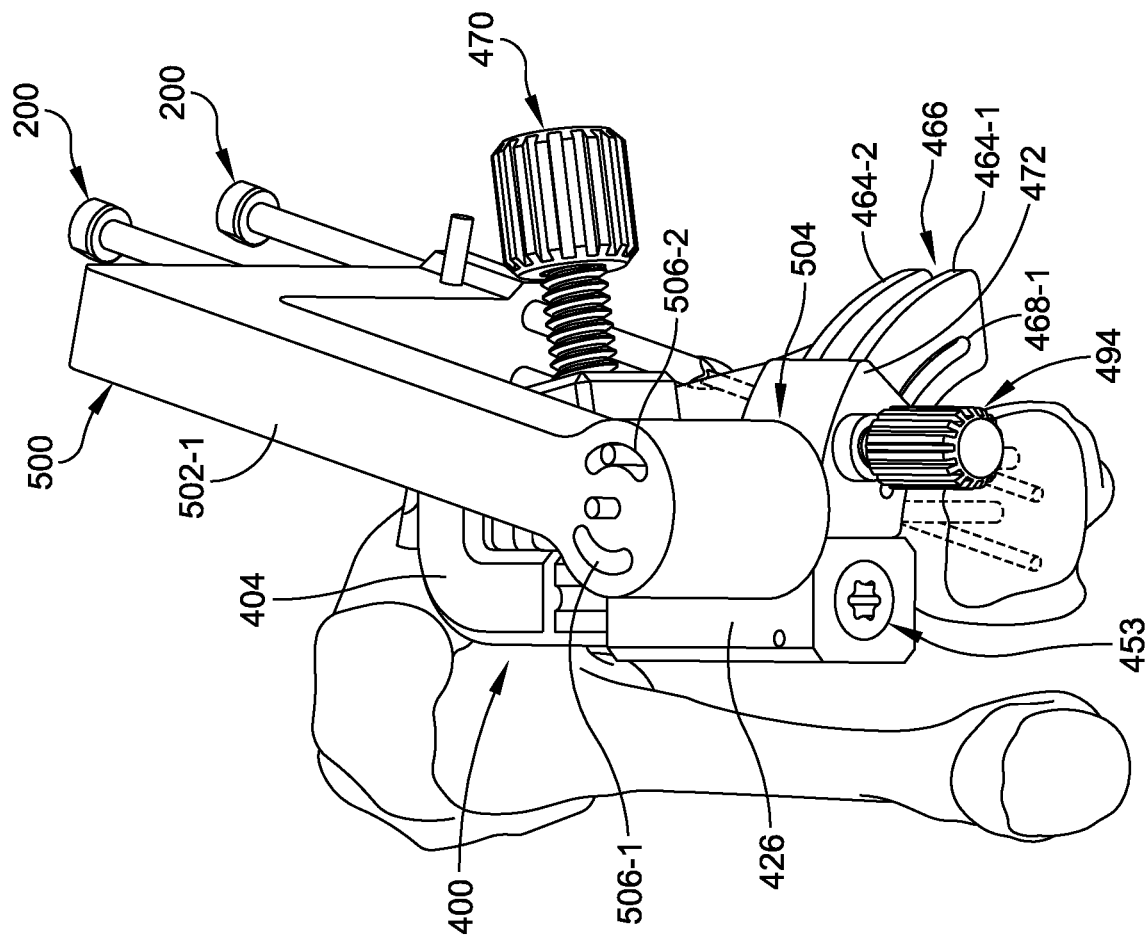
FIG. 52A is a front side elevational view of the assemblage of the base and targeting guide shown in FIGS. 50 and 51 coupled to bone in accordance with some embodiments.
Figure 52B:
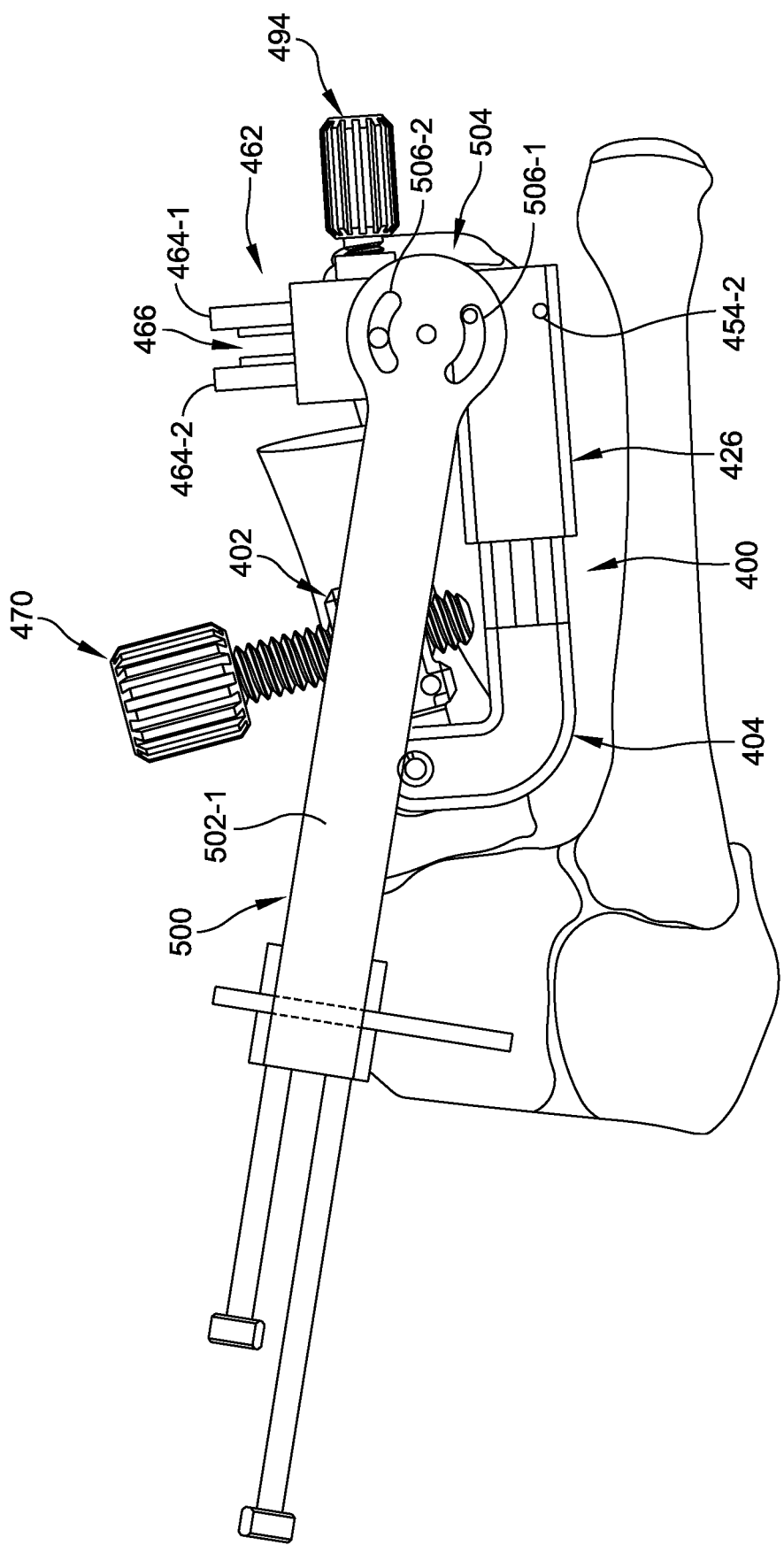
FIG. 52B is a side view of the assemblage of the base and targeting guide shown in FIGS. 50 and 51 coupled to bone in accordance with some embodiments.
Figure 53:
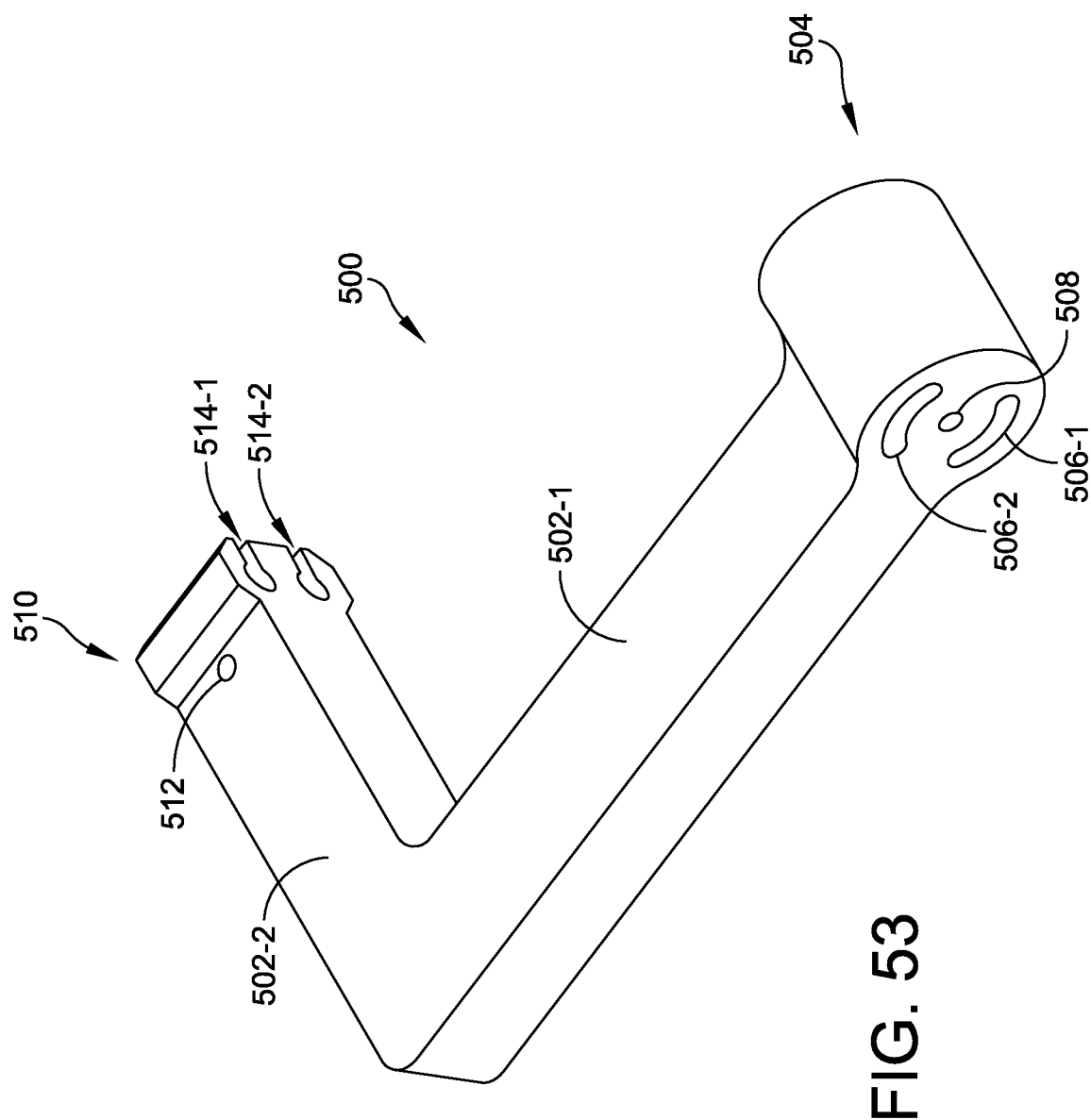
FIG. 53 is an isometric view of a targeting guide in accordance with some embodiments.

FIGS. 49 and 50 show the base 400 assembled and coupled to bone, and FIGS. 51-52B show a targeting guide 500 coupled to the base 400. Various views of the targeting guide 500 are shown in FIGS. 53-55. Referring first to FIG. 53, targeting guide 500 includes a body 502 having first and second arm portions 502-1, 502-2 (collectively, "arms 502") that diverge from one another. Arm 502-1 terminates at a coupling end 504, and arm 502-2 terminates at a targeting end 510.

Coupling end 504 defines one or more slots 506-1, 506-2 (collectively, "slots 506"), which may have arcuate shapes, and a hole 508. Slots 506 and hole 508 are sized and configured to receive a fixation element, such as a k-wire or pin, therein as best seen in FIG. 51. With a fixation element received within hole 508 and at least one of the slots 506, the targeting guide 500 may be able to pivot within a certain pre-defined range (i.e., the range provided by the length of the slots 506). A person of ordinary skill in the art will understand that the targeting guide 500 could be provided with only a hole 508, which would enable the targeting guide to pivot in a complete circle. Alternatively, one could insert a fixation element only into hole 508 to achieve the same function.

Targeting end 510 includes a first hole that extends through arm 502-2 in a first direction and one or more slots/holes 514-1, 514-2 (collectively, "slots 514," "holes 514," or "slots/holes 514") that extend in a second direction, which may be different from the first direction (e.g., oblique or perpendicular). Slots/holes 514 are sized and configured to receive a fixation element, such as a k-wire or pin therein. In some embodiments, slots/hole 514 is sized and configured to receive sleeve 200, which itself defines a hole 202 sized and configured to receive a fixation element as described above. Hole 512 is sized and configured to receive a k-wire or pin therein for securing the targeting guide 500 to a bone in a similar manner as hole 196 described above.

The function of base 400 and targeting guide 500 is similar to the function of base 100 and targeting guide 180 described above. One difference is due to the presence of the extension 462, which enables the mounting member 472, which supports targeting guide 500, to slide in an arcuate manner. In some embodiments, the arc is swept about an axis of the bone portion to which the base 400 is coupled.

FIGS. 56-76 illustrate another example of a system in accordance with some embodiments. The system shown in FIGS. 56-76 also may include a base 600 and a targeting guide 700. Referring first to FIGS. 57-63, base 600 includes a first body component 602, which includes a pair of divergent legs 604-1, 604-2 (collectively, "legs 604"). Leg 604-1 extends from a from second leg 604-2 and terminates at end 606. One or more slots 608-1, 608-2 (collectively, "slots") extend lengthwise along leg 604-1. The end 606 defines a hole 610, which may be threaded along at least a part of its length. Hole 610 extends lengthwise through leg 604-1. The opposite end of the hole 610 (shown in FIG. 63) may have an enlarged diameter to form a clearance area 612 as best seen in FIG. 63.

Leg 604-2 extends away from leg 604-1 and terminates at end 614. End 614 defines an opening 616. As described in greater detail below, opening 616 is sized and configured to at least partially receive second component 620 of body 600. As best seen in FIGS. 60 and 61, a hole 618 is formed at the opposite end of the opening 616 such that hole 618 communicates with opening 616.

FIGS. 64-67 illustrate one example of a second component 620 of body 600 in accordance with some embodiments. Component 620 also includes a pair of divergent legs 622-1, 622-2 (collectively, "legs 622"). Leg 622-1 extends away from leg 622-2 and terminates at end 624. One or more holes 626-1, 626-2 (collectively, "holes 626") extend through leg 622-1 from a first side 628 to a second side 630.

Holes 626 are sized and configured to receive a fixation element, e.g., a k-wire or pin, as described in greater detail below.

Figure 67:
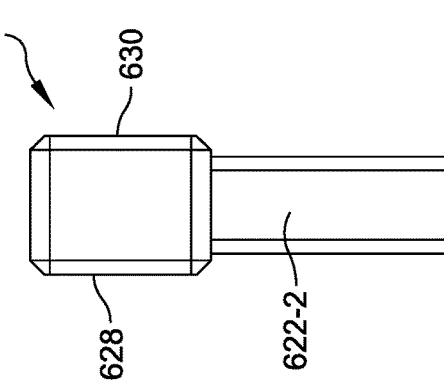
FIG. 67 is a front side view of the component shown in FIG. 64 in accordance with some embodiments.
Figure 64:
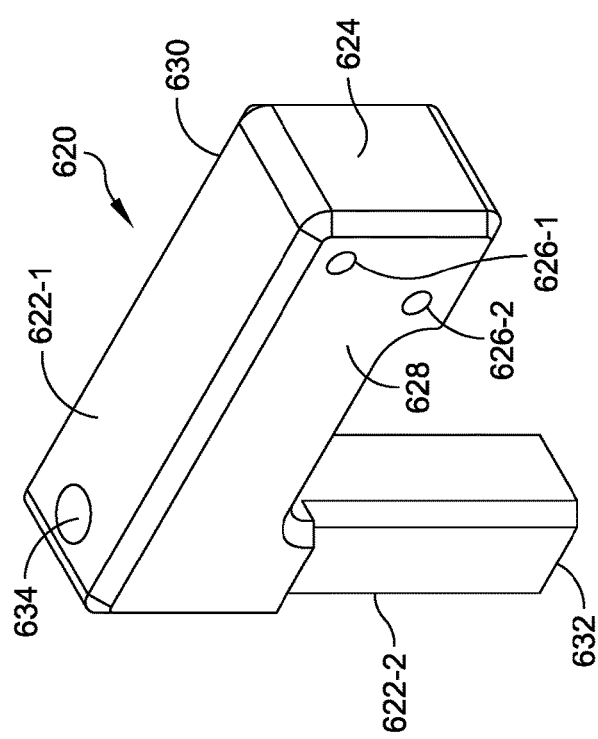
FIG. 64 is an isometric view of another component of the base shown in FIG. 57 in accordance with some embodiments.
Figure 66:
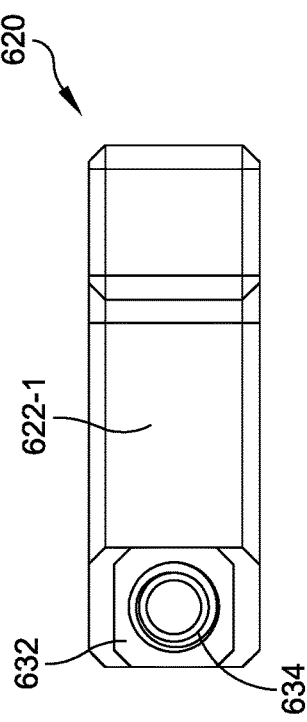
FIG. 66 is a bottom side view of the component shown in FIG. 64 in accordance with some embodiments.
Figure 70:
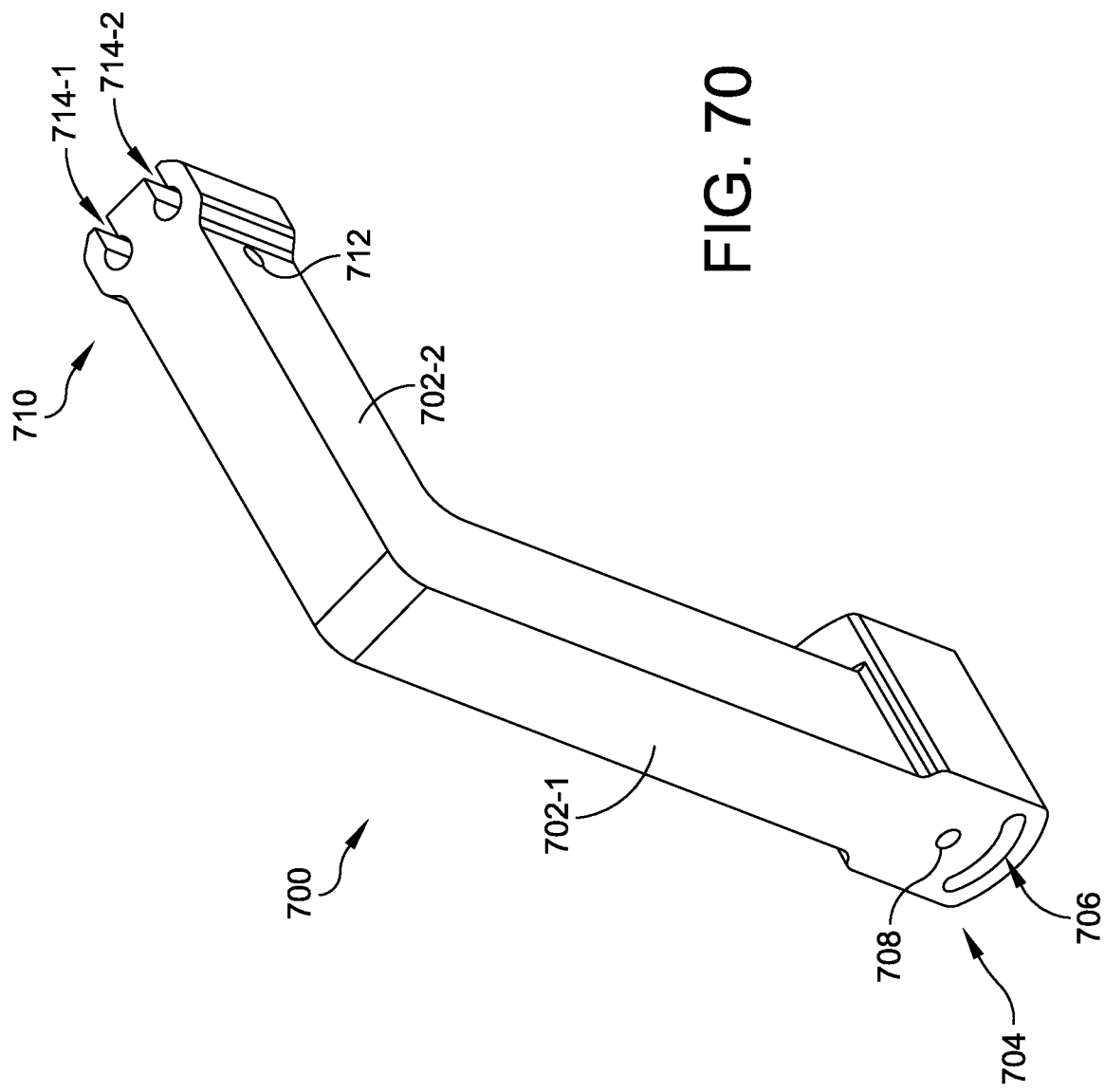
FIG. 70 is an isometric view of a targeting guide in accordance with some embodiments.
Figure 71:
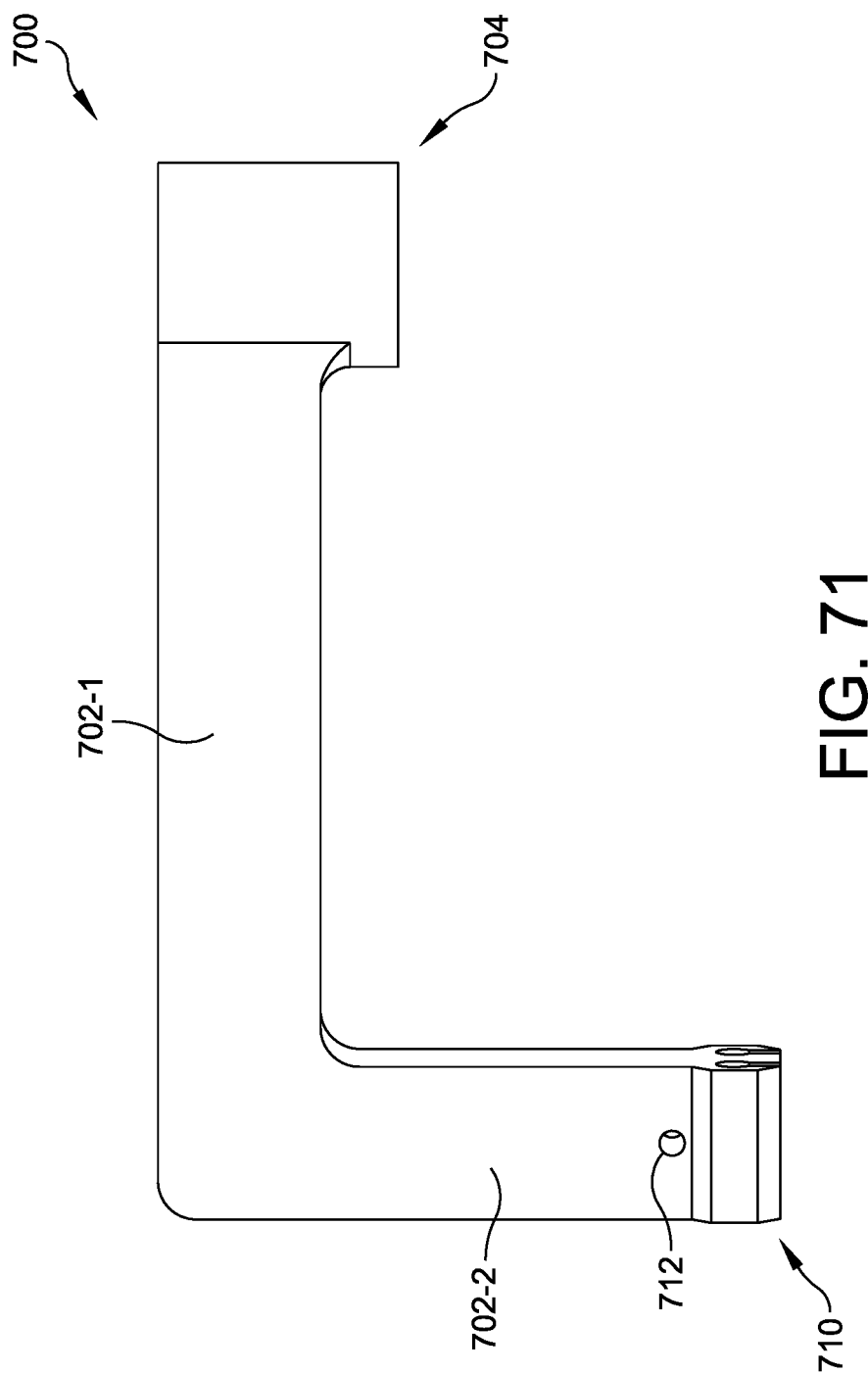
FIG. 71 is a side view of the targeting guide shown in FIG. 70 in accordance with some embodiments.
Figure 73:
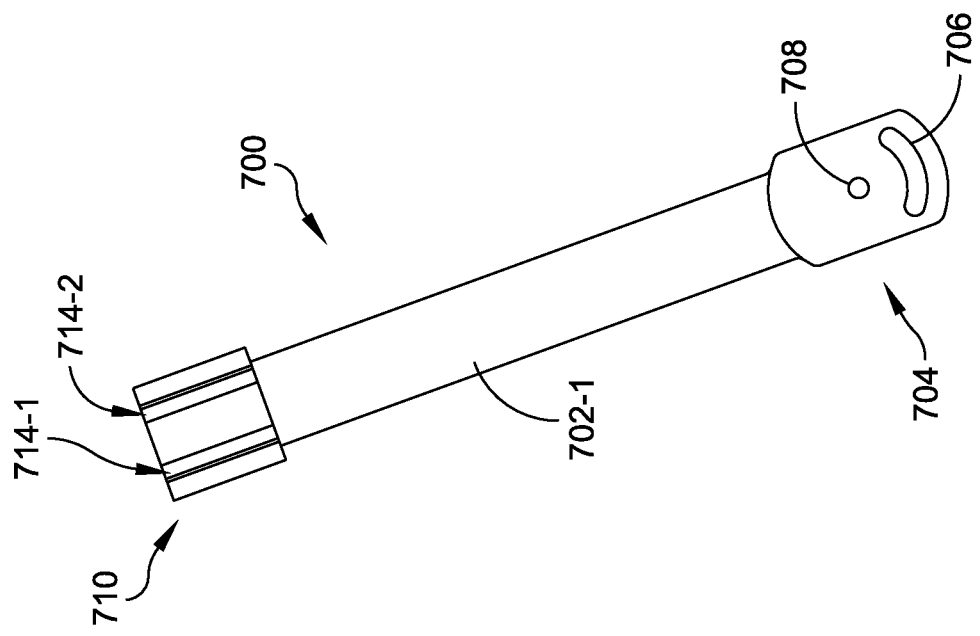
FIG. 73 is a bottom side view of the targeting guide shown in FIG. 70 in accordance with some embodiments.
Figure 72:
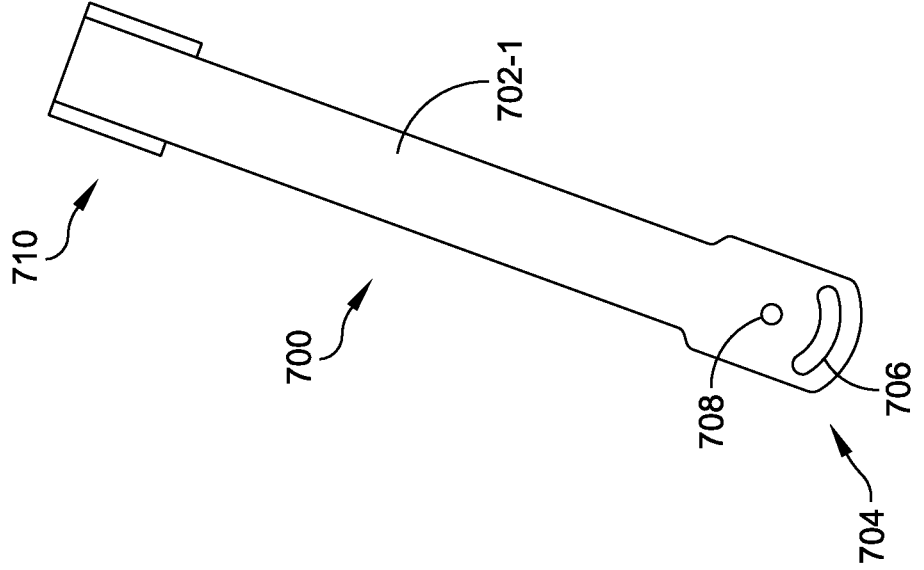
FIG. 72 is a top side view of the targeting guide shown in FIG. 70 in accordance with some embodiments.
Figure 74:
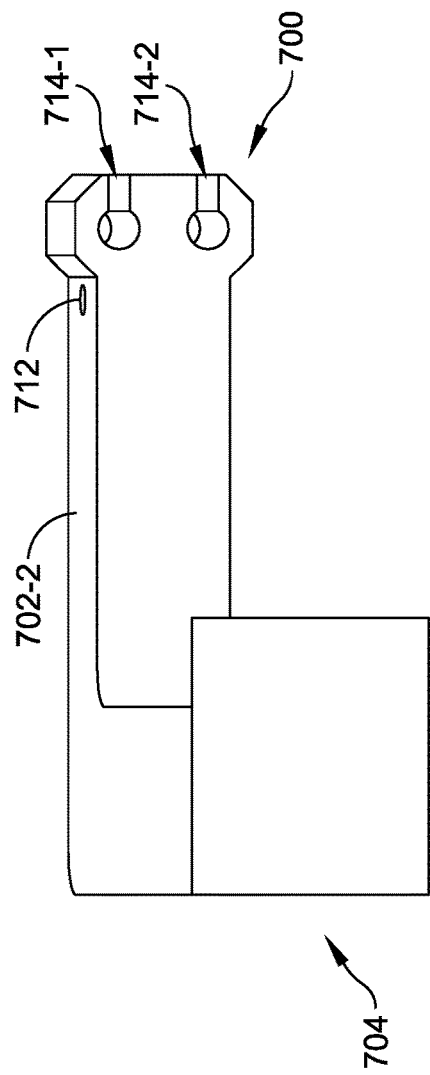
FIG. 74 is a rear side perspective view of the targeting guide shown in FIG. 70 in accordance with some embodiments.
Figure 75:
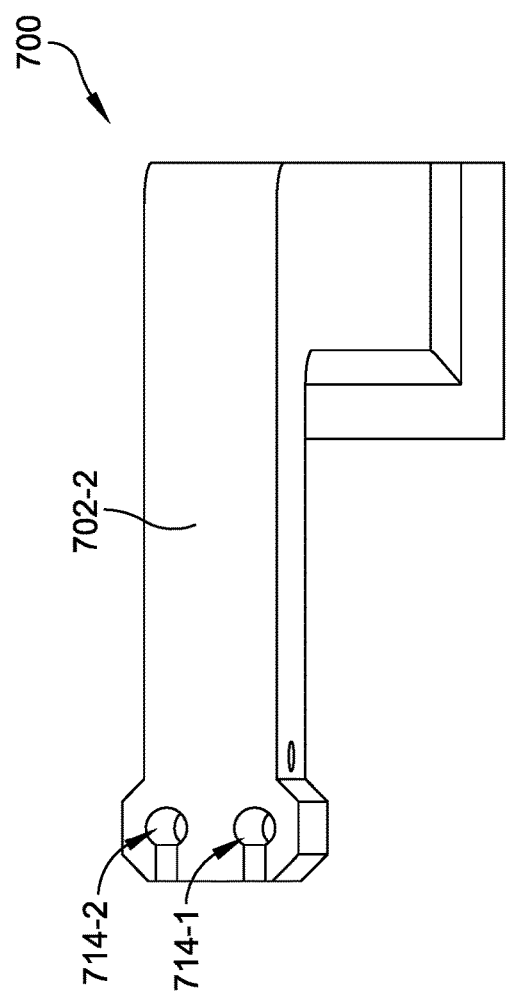
FIG. 75 is a front side perspective view of the targeting guide shown in FIG. 70 in accordance with some embodiments.

Leg 622-2 extends away from leg 622-1 and terminates at end 632. As best seen in FIGS. 64 and 67, leg 622-2 may be smaller in a width and thickness dimension than leg 622-1. The reduced dimensions of leg 622-2 enables it to be received within opening 616 defined by leg 604-2 of component 602. End 632 defines a hole 634 that extends lengthwise through leg 622-2. At least a portion of hole 634 may be threaded.

FIGS. 68 and 69 illustrate examples of two adjustment bolts 640, 650 that may be used with base 600. Referring first to FIG. 68, adjustment bolt 640 includes a threaded portion 642 and a head 644, which may have a larger cross-sectional diameter than threaded portion 642. Head 644 may define a circumferential slot 646 sized and configured to receive cross-pins 638-1, 638-2 (collectively, "cross-pins 638") as shown in FIG. 68 and described in greater detail below.

Adjustment bolt 650 depicted in FIG. 69 may include an elongate threaded stem 652 and a head 654. Head 664 may be detached from stem 652 as shown in FIG. 69 for reasons described below. Stem 652 extends from a coupling end 654 to a leading end 656. Coupling end 654 is shown having an engagement mechanism 658, which is shown as being a rectangular block that is sized and configured to engage a corresponding recess 672 (not shown) defined by head 664. Leading end 656 may include a pair of spaced apart circumferential flanges 660-1, 660-2 (collectively, "flanges 660"). Flanges 660 are spaced apart from one another to provide a gap 662 that is sized and configured to receive a fixation element, such as a k-wire or pin, therein as described in greater detail below.

Head 664 may have a cylindrical shape extended from a first end 666 to a second end 668. An driver engagement feature 670 may be defined by the first 666 for being engaged by a driving tool, such as a torx driver, screw driver, or hex key, as will be understood by one of ordinary skill in the art. The second end 668 may define a recess 672 (not shown) sized and configured to receive the engagement mechanism 658 of stem 652. In some embodiments, recess 672 is configured to receive engagement mechanism 658 via a press-fit engagement, although one of ordinary skill in the art will understand that other type of fits (e.g., slip fit) and mechanical engagements (e.g., cross-pins or set screws) may be used to couple the head 664 to stem 652.

Referring again to FIG. 57, the assembly of base 600 is described. The coupling end 654 of stem 652 of adjustment bolt 650 is inserted into clearance hole 612 of body component 602 until it emerges from hole 610. Head 664 of adjustment bold 650 is then coupled to stem 652 through the combination of engagement mechanism 658 and recess 672. The threads of stem 652 engage the threads of hole 610 such that rotation of bolt 650 results in bolt 650 translating along the length of leg 604-1.

Leg 622-2 of component 620 is received within opening 616 of leg 604-2, and adjustment bolt 640 is inserted into hole 618 defined by component 602 and is threaded into hole 634 defined by leg 622-2 of component 620. The head 644 of adjustment bolt 640 is inserted into component 602 until the circumferential slot 646 is aligned with one or more holes 636-1, 636-2 (collectively, "holes 636") defined by component 602. Cross-pins 638 are inserted into holes 636 to couple adjustment bolt 640 to component 602. As will be understood by one of ordinary skill in the art, the cross-pinning of adjustment bolt 640 to component 602 may used to secure other adjustment bolts to components described herein to the extent it is not expressly disclosed above. Rotation of adjustment bolt 640 causes leg 622-2 to translate along the length of leg 604-2.

Figure 56:
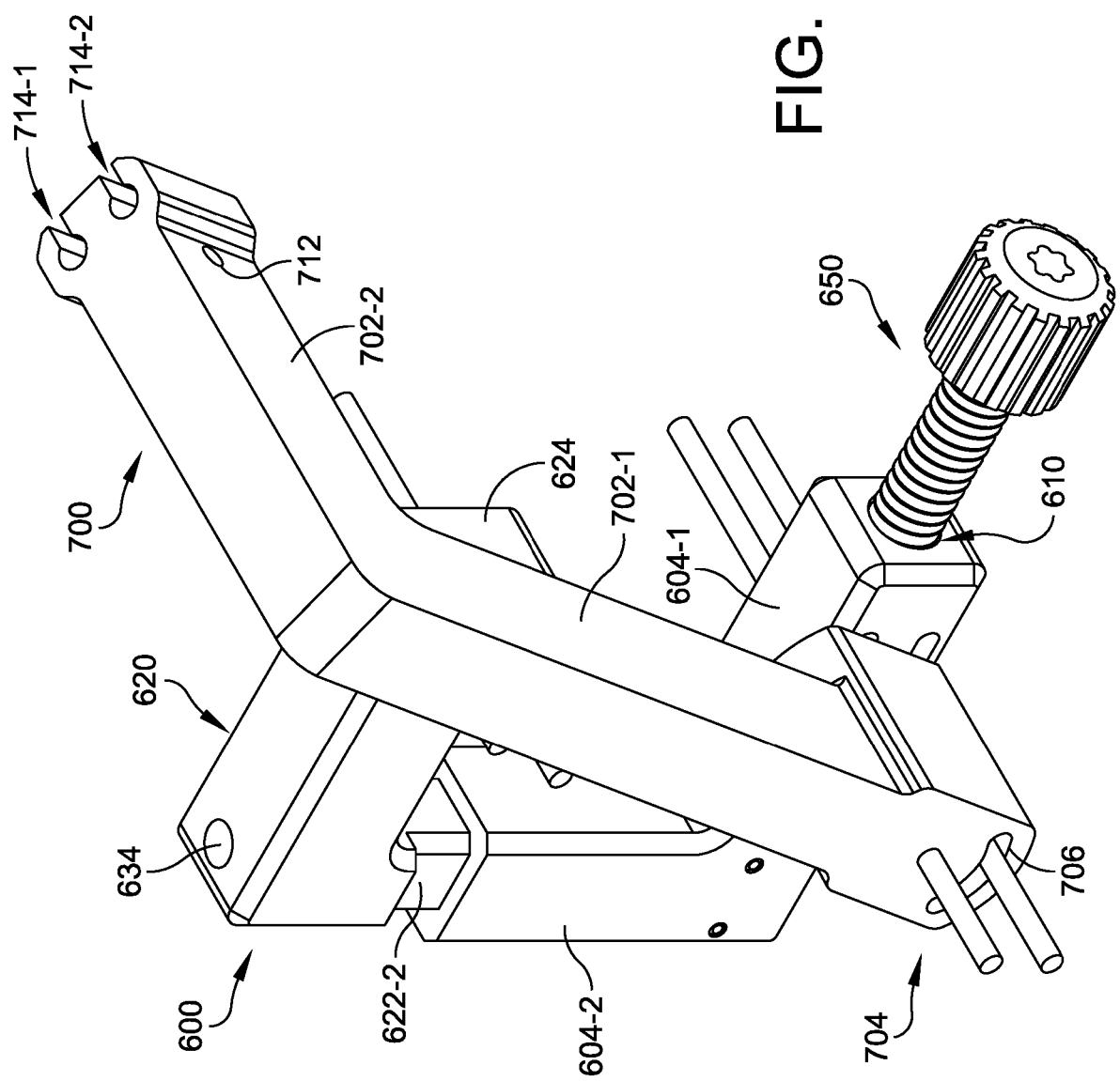
FIG. 56 is an isometric view of another example of a system in accordance with some embodiments.
Figure 57:
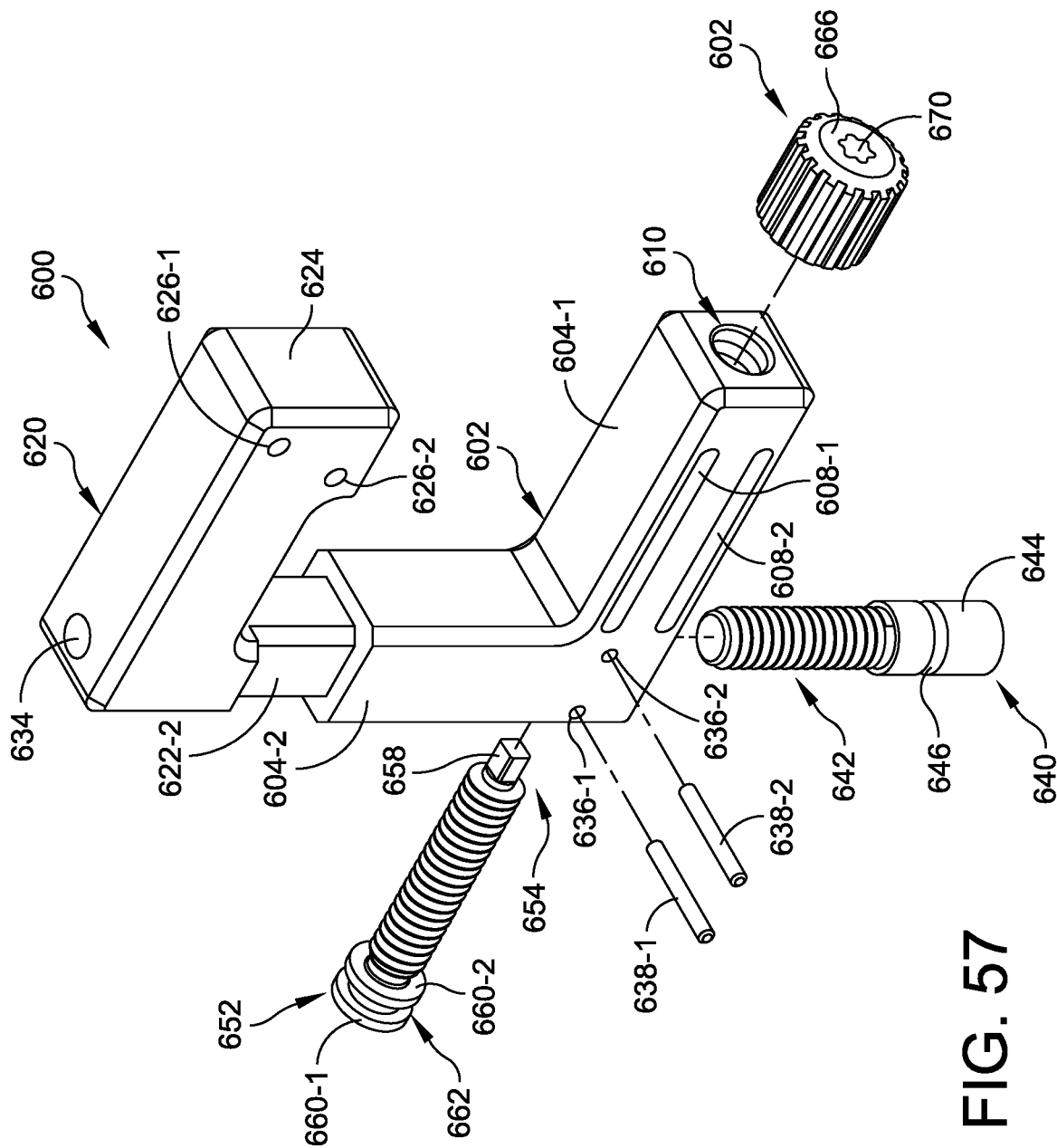
FIG. 57 is a partially exploded view of the base of the system shown in FIG. 56 in accordance with some embodiments.
Figure 59:
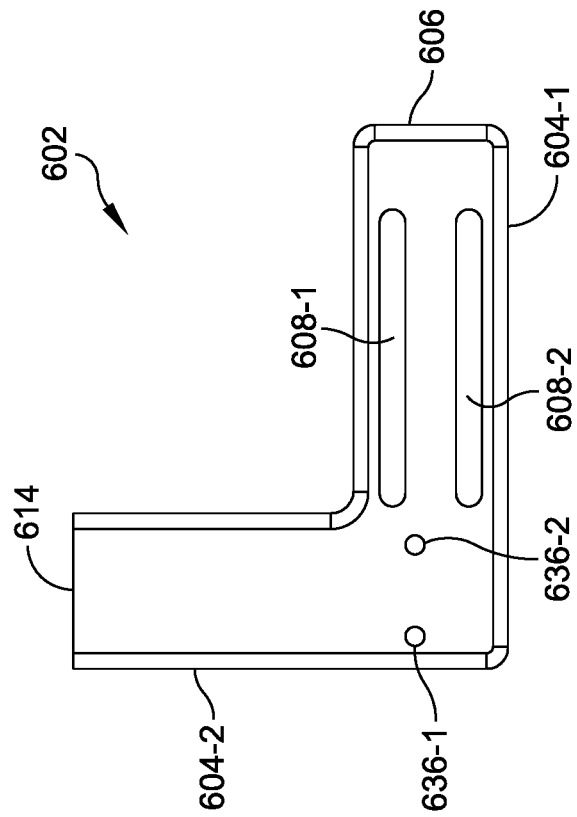
FIG. 59 is a side view of the component shown in FIG. 58 in accordance with some embodiments.
Figure 58:
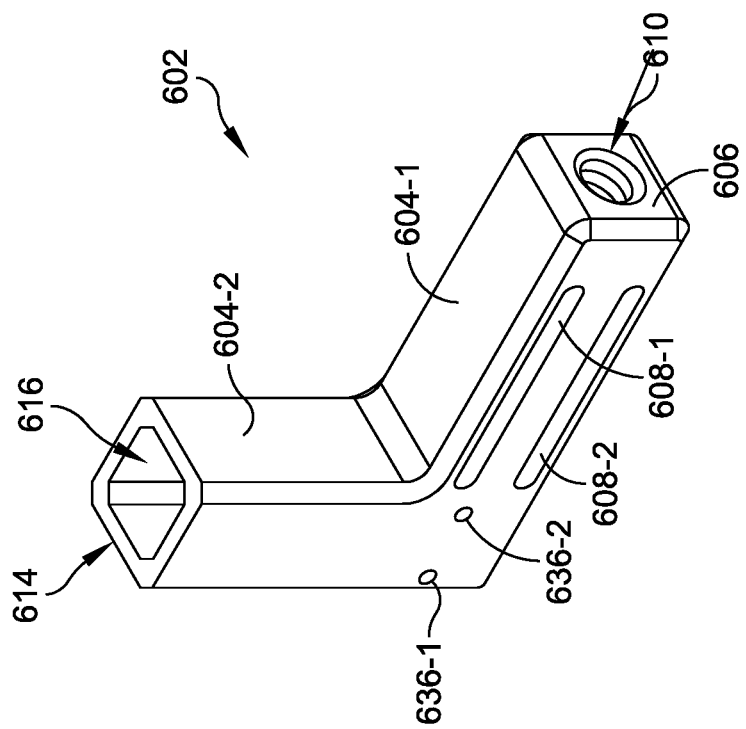
FIG. 58 is an isometric view of a first component of the base shown in FIG. 57 in accordance with some embodiments.
Figure 65:
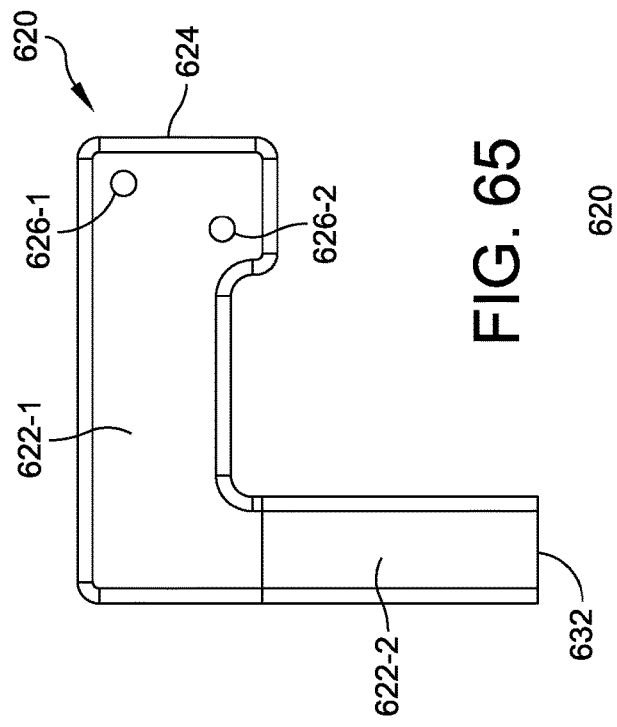
FIG. 65 is a side view of the component shown in FIG. 64 in accordance with some embodiments.

As shown in FIG. 56, a targeting guide 700 may be used in connection with base 600. While targeting guide 700 is described to be used with base 600, one of ordinary skill in the art will understand that base 600 may be used with the other targeting guides described herein, and targeting guide 700 may be used with other bases.

FIGS. 70-75 provide various views of targeting guide 700. Targeting guide 700 may include a pair of divergent arms 702-1, 702-2 (collectively, "arms 702"). Arm 702-1 extends from arm 702-2 and terminates in a coupling end 704. Coupling end 704 defines a one or more slots 706 and one or more holes 708. Both hole 706 and slot 708 are sized and configured to receive a fixation element, such as a k-wire or pin, therein as described in greater detail below.

Arm 702-2 extends from arm 702-1 and terminates in a targeting end 710.

Targeting end 710 defines one or more guide slots or holes 714-1, 714-2 (collectively, "slots 714" or "holes 714"). In some embodiments, holes 714 extend parallel to the length of arm 702-1. Targeting end 710 may also define one or more holes 712 that extends through arm 702-2. In some embodiments, hole 712 is non-parallel to holes 714. For example, hole 712 may be extend perpendicular or at an oblique angle relative to the direction of holes 714.

In use, base 600 is placed over a bone, such as a first metatarsal, and fixation elements P1, P2 are inserted through holes 626 defined by component 620 and into bone. Fixation elements P3, P4 may also be inserted through slots 608 defined by component 602. The fixation elements P3, P4 passed through slots 608 are inserted such that they are received within the gap 662 between flanges 660 of fixation bolt 650 that is disposed within arm 604-1 of component 602 and into bone as best seen in FIG. 76. In some embodiments, the fixation components P3, P4 passed through slots 608 are received within a metatarsal head. As described above, the base 600 may be coupled to the bone before or after the bone is segmented.

Once the bone is segmented, the base 600 may be used to distract or compress the bone segments relative to one another (e.g., move in a lengthwise direction of the bone) by rotating adjustment bolt 640. Additionally or alternatively, base 600 may be used to move the bone segments in a medial-lateral direction relative to one another using adjustment bolt 650. More particularly, rotation of adjustment bolt 650 advances or retracts the bolt 650 relative to arm 604-1. Due to the engagement of the fixation elements P3, P4 within gap 662, the rotation of bolt 650 also moves the fixation elements P3, P4 and bone attached to the fixation elements P3, P4.

Targeting guide 700 is placed relative to base 600 by engaging fixation elements P3, P4. More particularly, fixation element P3 is received within hole 708, and fixation element P4 is received within slot 706. In some embodiments, coupling end 704 of targeting guide 700 abuts leg 604-1 as shown in FIG. 56. Targeting guide 700 may be pivoted about fixation element P3 received within hole 708 while the presence of fixation element P4 limits the amount of rotation of targeting guide 700 as will be understood by one of ordinary skill in the art.

As described above with respect to the other embodiments, the targeting guide 700 may be used to receive fixation elements (e.g., pins or k-wires) within slots 714, which are used to fix the bone segments relative to one another. In some embodiments, guide sleeves 200 are inserted into slots 714 and used to guide the fixation elements as described herein.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system, comprising:
a base including first and second members that are coupled together in a pivoting arrangement, the first member including a first hole for receiving a first fixation element for coupling the first member to a first bone portion and a second hole for receiving an adjustment member for adjusting an angle between the first and second members, the second member having an adjustable length and defining at least one hole for receiving at least one second fixation element for coupling the second member to a second bone portion; and
a targeting member extending from a first end to a second end so as to be configured to be positioned relative to the base, the targeting member defines a first hole adjacent to the first end for receiving one of the at least one second fixation elements and further defines at least one hole for guiding at least one third fixation element into engagement with the first and second bone portions that is disposed adjacent to the second end of the targeting member.

2. The system of claim 1, wherein the at least one hole includes a pair of parallel holes.

3. A system, comprising:
a base including first and second members that are coupled together in a pivoting arrangement, the first member including a first hole for receiving a first fixation element for coupling the first member to a first bone portion and a second hole for receiving an adjustment member for adjusting an angle between the first and second members, the second member having an adjustable length and defining at least one hole for receiving at least one second fixation element for coupling the second member to a second bone portion wherein the second member includes a first component and a second component that are adjustable relative to one another, further wherein the second component defines an opening sized and configured to receive at least a portion of the first component therein; and
a targeting member configured to be positioned relative to the base, the targeting member defining at least one hole for guiding at least one third fixation element into engagement with the first and second bone portions.

4. The system of claim 3, wherein the first component is coupled to the first member and the second component defines the at least one hole for receiving at least one second fixation element.

5. The system of claim 3, wherein the second component defines a hole sized and configured to receive a second adjustment member for adjusting the length of the second member.

6. A method, comprising:
inserting a first fixation element through a first hole defined by a first member of a base of a tool;
inserting a second fixation element through a second hole defined by a second member of the base of the tool;
adjusting an angle between the first member and the second member with a first adjustment member;
adjusting a length of the second member with a second adjustment member;
positioning a targeting member relative to the tool such that the first fixation element is at least partially received within a first hole defined adjacent to a first end of the targeting member; and inserting at least one third fixation element through at least one third hole defined adjacent to a second end of the targeting member.

7. The method of claim 6, wherein adjusting an angle between the first member and the second member adjusts a position of a first bone relative to a second bone.

8. The method of claim 6, wherein adjusting a length of the second member adjusts a position of a first bone relative to a second bone.

9. The method of claim 6, wherein the at least one third fixation element extends through a first bone that is coupled to the first member of the base and into a second bone that is coupled to the second member of the base.

* * * * *